(12) United States Patent  (10) Patent No.: US 9,131,855 B2
McEowen  (45) Date of Patent: Sep. 15, 2015

(54) MULTIPARAMETER WHOLE BLOOD MONITOR AND METHOD

(75) Inventor: Edwin L. McEowen, Columbia City, IN (US)

(73) Assignee: New Paradigm Concepts, LLC., Fort Wayne, IN (US)

( * ) Notice: Subject to any disclaimer, the term of this patent is extended or adjusted under 35 U.S.C. 154(b) by 709 days.

(21) Appl. No.: 12/501,730

(22) Filed: Jul. 13, 2009

(65) Prior Publication Data

US 2009/0270695 A1  Oct. 29, 2009

Related U.S. Application Data

(60) Division of application No. 11/223,406, filed on Sep. 9, 2005, now Pat. No. 7,559,894, which is a continuation-in-part of application No. 10/944,161, filed on Sep. 17, 2004, now abandoned.

(60) Provisional application No. 60/504,295, filed on Sep. 18, 2003.

(51) Int. Cl.
*A61B 8/00* (2006.01)
*A61B 5/00* (2006.01)
(Continued)

(52) U.S. Cl.
CPC ............. *A61B 5/02055* (2013.01); *A61B 5/021* (2013.01); *A61B 5/024* (2013.01); *A61B 5/02007* (2013.01); *A61B 5/0215* (2013.01); *A61B 5/02028* (2013.01); *A61B 5/0285* (2013.01); *A61B 5/02116* (2013.01); *A61B 5/02125* (2013.01); *A61B 5/1459* (2013.01); *A61B 5/14535* (2013.01); *A61B 5/14546* (2013.01); *A61B 5/14551* (2013.01);
(Continued)

(58) Field of Classification Search
CPC ............. A61B 5/02055; A61B 5/0285; A61B 5/02007; A61B 5/6817; A61B 5/021; A61B 5/14551; A61B 5/1459
USPC .................. 600/438, 466–470, 481–504, 586
See application file for complete search history.

(56) References Cited

U.S. PATENT DOCUMENTS 4,600,855 A * 7/1986 Strachan ........................ 310/338
4,733,669 A * 3/1988 Segal ............................. 600/585
(Continued)

FOREIGN PATENT DOCUMENTS

WO    WO 2005/081185 A1    9/2005

OTHER PUBLICATIONS

Watenpaugh and Hargens, (1996); The cardiovascular system in microgravity; Handbook of Physiology-Environmental Physiology, pp. 631-674.
(Continued)

*Primary Examiner* — Patricia Mallari
*Assistant Examiner* — Tiffany Weston
(74) *Attorney, Agent, or Firm* — Barnes & Thornburg LLP

(57) ABSTRACT

The present invention provides an apparatus and methods for continuous intravascular measurement of whole blood concentration, blood pressure, and pulse pressure. The intravascular catheter incorporates a sensor to measure whole blood sound velocity, attenuation, backscatter amplitude, and blood flow velocity and also incorporates existing technologies for multiple physiologic measurements of whole blood. Pulse wave velocity and wave intensity are derived mathematically for purposes of estimating degree of local vascular tone.

10 Claims, 7 Drawing Sheets

(51) Int. Cl.

| | |
|---|---|
| *A61B 5/0205* | (2006.01) |
| *A61B 5/02* | (2006.01) |
| *A61B 5/021* | (2006.01) |
| *A61B 5/0215* | (2006.01) |
| *A61B 5/024* | (2006.01) |
| *A61B 5/0285* | (2006.01) |
| *A61B 5/145* | (2006.01) |
| *A61B 5/1455* | (2006.01) |
| *A61B 5/1459* | (2006.01) |
| *A61B 8/06* | (2006.01) |
| *A61B 8/12* | (2006.01) |
| *A61B 5/03* | (2006.01) |

(52) U.S. Cl.
CPC ............... *A61B5/412* (2013.01); *A61B 5/6817* (2013.01); *A61B 8/06* (2013.01); *A61B 8/12* (2013.01); *A61B 5/03* (2013.01); *A61B 2560/0252* (2013.01); *A61B 2560/0257* (2013.01)

(56) References Cited

U.S. PATENT DOCUMENTS

| | | | | |
|---|---|---|---|---|
| 5,309,916 | A | * | 5/1994 | Hatschek ...................... 600/485 |
| 5,339,816 | A | * | 8/1994 | Akamatsu et al. ............ 600/455 |
| 5,453,576 | A | | 9/1995 | Krivitski |
| 5,935,066 | A | | 8/1999 | Harris |
| 2003/0176789 | A1 | * | 9/2003 | Kaplan ......................... 600/438 |
| 2005/0124905 | A1 | * | 6/2005 | Ogura .......................... 600/528 |
| 2005/0150309 | A1 | * | 7/2005 | Beard ........................ 73/861.18 |

OTHER PUBLICATIONS

Bakke, T., Gytre, T., Haagensen, A., & Giezendanner, L. (1975); Ultrasonic measurement of sound velocity in whole blood: A comparison between an ultrasonic method and the conventional packed-cell-volume test for hematocrit determination. *Scandinavian Journal of Clinical Laboratory Investigations*, 35(5), 473-478. Abstract retrieved Feb. 5, 2005, from PubMed database.

Harada, A., Okada, T., Sugawara, M., & Niki, K. (2000). Development of a non-invasive real-time measurement system of wave intensity; IEEE Ultrasonics Symposium.

Hinghofer-Szalkay, H., Haas, G., Oser, H., & Kenner, T. (1989). Monitoring fluid shifts in humans: Application of a new method. Aviation & Space Environmental Medicine, 60(1), 23-28. Abstract retrieved Dec. 5, 2003 from Pub Med database.

Kenner, T. (1996); The continuous measurement of blood density and its experimental and clinical application—a review. Retrieved Sep. 27, 2003, from http://www.kfunigraz.ac.at.

Millero, F.J. and Xu, Li; (Abstract) Comments on "On equations for the speed of sound in seawater" (1994), J. Acoust. Soc. Am. 95(5), pp. 255-275.

Quick, C.M., Berger, D.S., Hettrick, D.A., Noordergraaf, A.; True Arterial System Compliance Estimated From Apparent Arterial Compliance, Annals of Biomedical Engineering; Issue: vol. 28, No. 3; Date: Mar. 2000; pp. 291-301.

Dushaw, Brian D.; Worcester, Peter F.; Cornuelle, Bruce D.; Howe, Bruce M.; On equations for the speed of sound in seawater; The Journal of the Acoustical Society of American; Jan. 1993—vol. 93, Issue 1, pp. 255-275.

Akimitsu Harada, Takashi Okada, Kiyomi Niki, Dehua Chang and Motoaki Sugawara; New Methods of One-point Measurement of Pulse Wave Velocity; 2002 IEEE Ultrasonics Symposium.

Hinghofer-Szalkay, H.; Continuous blood densitometry—fluid shifts after graded hemorrhage in animals; published Jan. 1, 1986.

Supplementary Partial European Search Report; May 3, 2012.

Yoonkee, Kim, et al: "Sensing the Properties of Liquids with Doubly Rotated Resonators"; 1998 IEE International Frequency Control Symposium; US Army Communications—Electronics Command; Attn: AMSEL-RD-C2-TP; Fort Monmouth, NJ 07703; J.Vig@ieee.org.

\* cited by examiner

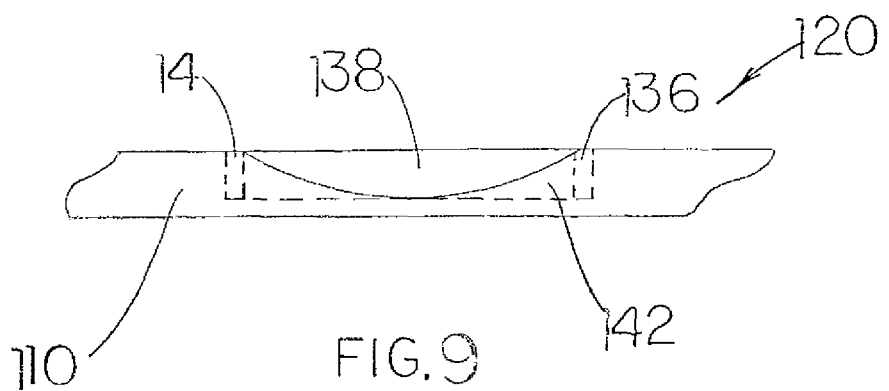

MULTIPARAMETER WHOLE BLOOD MONITOR AND METHOD

RELATED APPLICATIONS

This application is a Divisional of U.S. patent application Ser. No. 11/223,406, filed on Sep. 9, 2005, entitled Multiparameter Whole Blood Monitor and Method, now U.S. Pat. No. 7,559,894, which was a continuation-in-part of U.S. patent application Ser. No. 10/944,161 filed on Sep. 17, 2004, entitled Noninvasive Vital Sign Measurement Device, which claimed the benefit of U.S. Provisional Application Ser. No. 60/504,295, filed on Sep. 18, 2003. These applications are hereby incorporated by reference in their entireties.

BACKGROUND AND SUMMARY

The National Trauma Data Bank Report for 2004 describes 576,247 hospital admissions for trauma between 1999 and 2004. Of these cases, 109,080 patients were admitted to the intensive care unit (ICU), 100,050 were taken directly to the operating room (OR), and 7878 died. The remaining 332,928 were admitted for general care. For many of these patients (especially for the ICU and OR patients) it was necessary to closely monitor the hematocrit with multiple phlebotomy blood samples within the first few hours. The key to providing optimal care for these challenging patients is for the trauma specialist to provide rapid therapeutic interventions based upon informed decision-making. The clinician's ability to deliver such quality care is based primarily on physical assessment skills, training, and experience, and secondly upon the degree of patient physiologic and hemodynamic data available at the moment of decision-making. There is a clear need for the clinician to have quantitative data to base his or her treatment decision.

The process of frequent phlebotomy consumes valuable emergency staff time and there can be substantial lag-time before results are available. Laboratory techniques have become more accurate and bedside devices have improved turn-around time for in vitro lab analysis, but these improvements have not alleviated the central problem of lack of real time information. The patient's condition may deteriorate within minutes, and reasons for the deterioration can be varied and not always obvious. Survival rates for such patients could be improved if needed data could be provided continuously, allowing better opportunity to act upon the vital information in a more timely manner. Patient monitoring methods have advanced over the decades with the development continuous arterial blood and oximetry pressure monitoring, but there remains no device that delivers other necessary physiologic data on a continuous basis. New Paradigm Concepts (NPC) proposes to remove uncertainty in realm of critical care medicine by developing a point-of-care continuous blood concentration monitor.

In the current practice of critical care medicine, the only patient parameters that are continuously monitored are the vital signs, pulse oximetry, and temperature. Aside from oximetry, the physiologic parameters are available only through phlebotomy sampling and laboratory analysis. The hemodynamic parameters, other than vital signs, are available only with central vascular catheterization in the ICU or the cardiac catheter laboratory. The availability of these continuous physiologic and hemodynamic parameters during patient resuscitation would improve the delivery of appropriate, timely, and cost effective patient care and, thereby, improve outcomes. Such continuous monitoring would also improve the ability of the critical care team to effectively care for multiple patients without the need for numerous and laborious repeat lab tests.

It is an object of the invention to accurately and continuously measure multiple blood parameters within a patient's artery or vein and to precisely trend and display these parameters in a way that is useful for medical clinician interpretation and decision-making.

It is an object of the invention to provide methods and apparatus to accurately and continuously measure blood density (concentration) and hematocrit. For simplicity, hematocrit heretofore will be referred to generally as hematocrit and hemoglobin (H/H).

It is an object of the invention to provide a mathematical relationship between the accuracy of the method of sound speed measurement of H/H and the serum protein content.

It is an object of the invention to provide a method and apparatus to continuously measure and trend pulse pressure (the difference between systolic and diastolic blood pressure).

It is an object of the invention to provide a method and apparatus to continuously and accurately measure and trend blood pressure (systolic, diastolic, mean arterial, and venous).

It is an object of the invention to provide a method and apparatus for blood volume estimation and precise trending.

It is an object of the invention to provide a method and apparatus for continuously and accurately measuring and trending local blood flow velocity.

It is an object of the invention to provide a method and apparatus for mathematical estimation and precise trending and display of an index of local peripheral resistance (LPR) otherwise known as local vascular tone (LVT).

It is an object of the invention to provide a precision temperature probe into the catheter for both sensor calibration and display of the results as a vital sign.

It is an object of the invention to incorporate any or all of the above methods and apparatus into a catheter that can be placed into a peripheral or central vein or artery to measure multiple blood parameters in situ and to display the results for the purposes of clinical interpretation and decision-making.

It is an object of the invention to incorporate into a catheter as many other existing technologies as possible for the purpose of providing continuous information about any blood parameters that are desirable to measure on a frequent basis during the care of a seriously ill or injured patient and to display the results for the purposes of clinical interpretation and decision-making.

Briefly, the present invention consists of a method of ultra-precise measurement of sound speed both intravascularly and non-invasively with the acoustic transducer(s) mounted non-invasively on opposite side of a blood vessel or artery or on an intravascular catheter. The catheter would be similar in length to that used for IV access or arterial line access, and construction would include a port for drawing blood samples or, in the venous application, for administering medications. The present invention provides an apparatus and methods for continuous intravascular measurement of whole blood concentration, blood pressure, and pulse pressure. The intravascular catheter incorporates a sensor to measure whole blood sound velocity, attenuation, backscatter amplitude, and blood flow velocity and also incorporates existing technologies for multiple physiologic measurements of whole blood. Pulse wave velocity and wave intensity are derived mathematically for purposes of estimating degree of local vascular tone. The uniqueness of the invention is in its use for monitoring patients continuously throughout their course of resuscitation and treatment in its novel ultrasound methods for accurate measurement of H/H, pulse pressure, and blood pressure, and in its incorporation of other technologies to provide a plethora of physiologic and hemodynamic data heretofore obtained only by complex invasive means.

Additional features and advantages of the gripper assembly will become apparent to those skilled in the art upon consideration of the following detailed description of the illustrated embodiment exemplifying the best mode of carrying out the gripper assembly as presently perceived.

BRIEF DESCRIPTION OF DRAWINGS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations or further modifications of the described embodiments, and any further applications of the principles of the invention as described herein are contemplated as would normally occur to one skilled in the art to which the invention relates.

FIG. 9 is a view like FIGS. 6, 7 and 8 of still another version of the new and improved multiparameter intravascular catheter vital sign measurement device of the invention showing a sender/receiver transducer and a reflector mounted in a notch cut into the side of the catheter with a membrane or diaphragm covering and sealing the notch forming a gas filled chamber pressure sensor.

DETAILED DESCRIPTION OF SELECTED EMBODIMENTS

Figure 1:
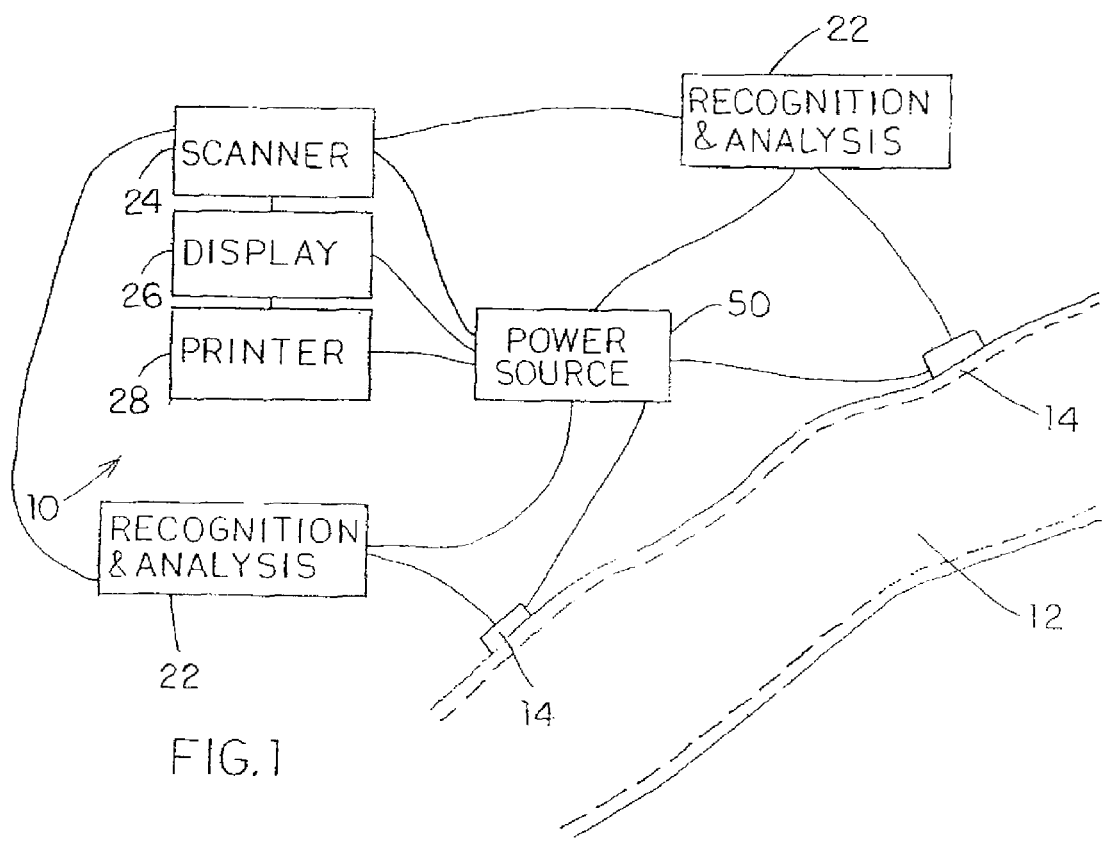
FIG. 1 is a diagrammatic view of a body part having the new and improved noninvasive vital sign measurement device of the invention attached thereto utilizing a spaced apart sender and receiver.

The new and improved noninvasive vital sign measurement device 10 of the invention is a medical device for supplying vital sign measurements for any purpose and in any setting where such information is useful to medical clinicians conducting physical examinations or monitoring patients (inpatient, outpatient, or ambulatory), whether in well-equipped hospitals, clinics, or on a battlefield. The invention would allow the monitoring of vital signs continuously. In the vascular application of the device, vital signs that can be measured would include arterial and venous blood pressure and pulse, blood flow velocity, and blood density. Peripheral vascular resistance could be calculated and displayed using data from the device. More conventional equipment could be mated with the device in order to continuously monitor such things as temperature and oxygen saturation. Other potentially measurable pressure parameters could include the extravascular space, intracranial space, intrathoracic (vascular, airway, and pleural) space, or any confined body cavity, depending upon the particular configuration of the device and where it is mounted upon or applied to the body. Examples of confined body cavities would include possibly the urinary bladder, gallbladder, intra-abdominal, ocular, and more probably extremity fascial compartments. Additional measurements that may be obtainable by the device could be other vascular parameters including possibly intracardiac chamber pressures and more possibly central venous pressures.

When arterial blood pressure is measured and monitored, both systolic and diastolic blood pressure should be monitored beat-by-beat. This information would be useful in evaluating routine vital signs, hypertension, hypotension, and shock from any cause. The instantaneous monitoring by the application of the invention would provide a means by which the effectiveness of pharmaceutical intervention and surgical intervention could be immediately assessed. Venous and extravascular space monitoring can be used to determine tissue perfusion and lymphatic obstruction, as well as the general state of hydration of the patient. Vascular monitoring will provide information regarding patient shock from any cause, e.g., sepsis, blood loss, and autonomic malfunction. Data from the combined monitoring of arterial pressure and blood flow could be used to calculate vascular resistance. For the clinician, knowing the level of vascular resistance and continuously monitoring blood pressure are key factors in determining not only the cause of shock but also the best course of treatment in each circumstance.

Intrathoracic measurements could include intrapulmonary and intracardiac, as well as pleural and pericardial space pressures. Measurement of large, medium, and small airway and alveolar space pressures would give physicians both diagnostic and treatment monitoring tools for acute and chronic lung disease. The device could be used to confirm endotrachial tube placement. Intrapleural pressure measurements would provide data for rapid diagnosis or confirmation of hemothorax and pneumothorax, and could be used in both hospital and prehospital settings to help determine the urgency with which these conditions should be treated.

Intracardiac pressure measurements would allow diagnosis of valvular failure, cardiomyopathy, congenital defects, myocardial ischemia/infarct, and congestive heart failure. Chamber pressure measurements together with echocardiogram data and pulmonary vascular readings would yield vital information regarding the etiology of any of the above maladies previously available only with cardiac catheterization.

More convenient and accurate ocular pressure measurement would allow physicians improved means of diagnoses and treatment monitoring of ocular diseases such as glaucoma.

Intracranial pressure measurements would most likely be extremely difficult because of signal attenuation through bone; however, if possible, it would give physicians a rapid estimate of tissue pressure, ventricular pressure, and vascular space pressure when dealing with patients suffering from head injury or stroke, and post-operative neurosurgical patients. It would also be useful in the diagnosis of such maladies as pseudotumor cerebri and hydrocephaly.

Currently, most all of the measurements above can be obtained accurately only by the use of expensive and/or invasive procedures. Sphygmomanometer blood pressure cuff readings are accurate in normal and high ranges, but cumbersome and slow, as well as painful for many patients. For automatic blood pressure cuff devices, the International Electrotechnical Commission has set international standards regarding strict limits on the pressure to which the cuff can be inflated. And, in order to avoid tissue damage and considerable discomfort to the patient, they have also set limits on the period of rapid inflation/deflation cycles. Blood pressure cuff readings are in fact contraindicated for post-mastectomy patients in the arm on the affected side. However, when vital signs are unstable or potent drugs are needed in order to maintain blood pressure, time-consuming invasive procedures are required for continuous monitoring. In the emergent setting, clinical decisions must often be made long before there is any x-ray or echocardiography evidence available and long before invasive vascular monitoring catheters can be inserted and calibrated.

Vital sign data which can be obtained by the device are useful in intensive care units, operating rooms, all prehospital settings, emergency departments, dialysis centers, medical practice offices, medical research, pulmonary and veterinary clinics, in military installations or on a battlefield, and in aerospace installations for monitoring pilots and astronauts at work. On an ambulatory basis, such data would also be very useful in everyday life and in the sports world. We currently have no convenient way to monitor the businessman, the homemaker, or the athlete in action.

The function of the device depends upon subtle, but measurable, changes in acoustic velocity that occur as a result of changes in density of the medium through which the sound wave is propagating. The noninvasive device would measure acoustic transit times, and thereby measure density within fluid or gas-filled body organs/structures/vessels. By monitoring transit times and minute shifts in transit time in rapid sequence (10 to 100 times per second) during all phases of systole and diastole, such measurements, if made with precision, would result in accurate, reliable, and continuous vital sign data.

In addition to arterial and venous pressure readings, this principle would in like manner apply to the measurement of pressure in gas-filled structures such as pulmonary airways and possibly the bowel lumen. Similarly, ocular, intrauterine, and possibly extremity compartment pressures would be amenable to measurement. Intracranial pressures may be measurable with this technique as well. The acoustic frequency specifications and configuration of the device would be altered according to the purpose at hand; e.g., airway pressure measurement would require much lower frequencies for better intrathoracic sound penetration and since acoustic velocity is much slower in gas than in fluid.

The measurements are based upon the characteristics of acoustic waves as they propagate through biologic tissue or fluids or gases. Since acoustic velocity increases with the density of the medium through which it is propagating, then there must be a measurable change in acoustic velocity through a fluid or gas-filled vessel, cavity, or compartment as the density within changes. Minute blood density fluctuations will occur as the blood pressure cycles between systole and diastole. Therefore, there must be a measurable change in the acoustic wave propagation velocity through the blood as the pressure changes. The common equation, V=D/T, indicates that changes in velocity (V) are inversely proportional to changes in transit time (T) over a fixed distance (D). If the measurements were done with precision, then the device output would consist of highly accurate, beat-by-beat digital pressure readings in the case of vascular application of the device.

The UNESCO equation describes the relationship between acoustic wave velocity and pressure in water. The equation also takes into account other factors that contribute to the density of the fluid, such as the salinity and the temperature. Although fluids (blood included) are considered incompressible, the equation shows that there should be minute but measurable changes in velocity associated with changes in pressure, even within the human blood pressure range of 0 to 300 mmHg.

To form theoretical support for this method, the space between two hypothetical transducers was assumed to be 10 cm. The UNESCO equation was then used to calculate acoustic velocity at pressure increments of 10 mmHg assuming fluid temperature is 37.degree. Celsius, salinity is 9 psu (practical salinity units) or ppt (parts per thousand), and variable pressure is expressed in kPa. Calculations using the formula V=D/T indicate that in order for the device to have precision to within 1 mmHg, it must be capable of detecting shifts in transit time of roughly 10 picoseconds. Trending of the pressure could be achieved by the detection of shifts of approximately 100 picoseconds.

Referring now to FIG. 1, the monitoring device 10 is shown attached to a body part 12 from which the blood pressure and other vital signs are monitored. Body part 12 can be any body part including the head, the neck, the chest, the abdomen, the arms, and the legs, to measure pressure in any blood vessel in good proximity to the skin's surface. Two transducers 14, 16 are spaced apart, longitudinally in line with a vessel, a specific and fixed distance, e.g., 10 cm, and applied to the skin using an acoustic conductive medium. By measuring the transit time of the acoustic signal between the two transducers 14, 16, the velocity of the sound wave through the tissue can be calculated using the equation V=D/T, where V equals the velocity; D equals the space between the transducers 14, 16; and T equals the time the signal takes to propagate (transit time) between the two transducers 14, 16. One transducer 14 (the sender) generates the input signal and the other transducer 16 (the receiver) generates the output signal.

Utilizing this pitch-catch method, with the two transducers 14, 16 both serving the dual function of sender and receiver, measurements of both upstream and downstream transit times would be achieved. Blood flow velocity would be calculated in a conventional manner using the difference between downstream and upstream transit times. Since transit time oscillations resulting from blood flow are magnitudes greater than transit time oscillations associated with cyclical pressure changes, these flow oscillations must be effectively cancelled out of the calculation by the summation of downstream and upstream transit times. The data resulting from this summation would reflect the effect of pressure fluctuations on transit times. The summation would magnify the observed systolic/diastolic shift in transit times by a factor of two while canceling the effect of blood flow. Also, this technique would reduce artifact resulting from body movement and intravascular turbulence. Mathematically this can be expressed as follows: $T_{total} = (T_{downstream} + T_{upstream})/2$ Factors determining total transit time are (1) acoustic velocity due to blood density, (2) acoustic velocity as it is influenced by blood flow and artifact produced by body movement and vascular turbulence, and (3) the velocity of the acoustic wave as it passes through the surface conductive medium and the skin and subcutaneous tissues. V.sub.total=V.sub.1+V.sub.2+V.sub.3

V.sub.3 (tissue and conductive medium contribution to velocity) will remain constant. V.sub.2 (blood flow and artifact contribution to velocity) can be readily measured and canceled out of the equation by summing the velocity in both directions, thereby eliminating its contribution to the equation. Therefore, V.sub.1 (density contribution to velocity) remains as the only variable factor when transit times are measured, and, within blood vessels, pressure will be the only density determining factor that fluctuates on a moment by moment basis. V.sub.total=V.sub.density+V.sub.constant Therefore: .DELTA.V.sub.total=.DELTA.V.sub.density Since density—as it is determined by the momentary values of hematocrit, salinity, and temperature—remains fixed, then it follows that any momentary velocity fluctuations are a result of fluctuations in pressure alone. Thus:
.DELTA.V.sub.density=/.DELTA.V.sub.pressure and therefore:
.DELTA.V.sub.total=.DELTA.V.sub.pressure Therefore, any momentary fluctuation in transit times will also be a result of fluctuations in pressure. These fluctuations in transit times can thus be expressed mathematically as:
.DELTA.T.sub.total=.DELTA.T.sub.pressure and since:
.DELTA.T.sub.total=(.DELTA.T.sub.downstream+.DELTA.T.sub.upstream)/2 then therefore:
.DELTA.T.sub.pressure=(.DELTA.T.sub.downstream+.DELTA.T.sub.upstream)/2

Signal processing and adequate sound conduction through the skin and subcutaneous tissues to and from the structure of interest are critical steps involved in ensuring the accuracy and reliability of the device. Factors such as incorrect device placement, obesity, and edema will interfere with acoustic conduction and possibly render the device ineffective. In an aerospace application or during sports participation, high G forces may effectively dislodge the device from its proper position. The use of bi-directional "pitch-catch" transducers will reduce the error resulting from imprecise device placement upon the body. This method will also likely reduce artifact from body movement.

The output signal would appear as an amplitude spike (buried within noise) that moves to and fro along the instrument's time scale indicating at its limits a systolic and diastolic transit time for each cycle. Shorter transit times are associated with the systolic pressure and longer transit times with the diastolic pressure. The point along the larger transit time scale where these minute pressure-related transit time shifts will be observed will drift as blood density drifts due to changing physiologic values such as hematocrit, salinity, and temperature. This drifting must be accounted for by the continuous and precise monitoring of blood density as it is affected by these varying physiologic values. This can be done using the precision acoustic transit time measurements described earlier, and it is essential for continuous calibration of the device as base-line drifting of blood density occurs.

Ideally, calibration measurements will be made by observing the density of venous blood while it is under the influence of zero increased vascular pressure, i.e., at atmospheric or ambient pressure. As the device operates in its vascular mode, continuous calibration and ultra-precision is the core of its design and function. To summarize, the core of the device design and function depends upon ultra-precision and continuous calibration for changes in temperature and also for changes in transducer separation distance (if not fixed by use of a rigid housing). (See page 34.)

According to the UNESCO equation, there is a 98.4 picosecond change in the transit time across a 10 centimeter distance for every 10 mmHg change in pressure. However, the variability of the above mentioned physiologic values may result in as much as several hundred nanoseconds of drift in transit times. According to the UNESCO equation, when salinity is fixed at 9 psu, a change in body temperature of 1 degree Celsius would alter transit time by about 75 nanoseconds (a scale that is magnitudes greater than transit time shifts resulting from incremental changes in pressure). Similarly, with temperature fixed at 37.degree. Celsius, alterations in salinity of only 0.1 psu would result in a change in transit time of about 4.25 nanoseconds. These values were calculated using velocity data obtained from the UNESCO equation at the National Physical Laboratories (NPL) interactive website and using the previously noted common equation, V=D/T. Such large scale changes in blood density would of course occur over a period of hours and not milliseconds and therefore should not affect momentary pressure readings. However, if blood density alterations are not monitored precisely and continuously, then the minute fluctuations in transit time related to pressure oscillations would have no baseline or frame of reference and would be useful only for pulse detection. Even trend monitoring would be difficult as such without a solid frame of reference.

Ideally, in order for the peak and trough (systolic and diastolic) density values to be meaningful, the measurement of baseline density must be performed within the observed fluid or gas when it is under zero increased pressure. In vivo, however, blood or other physiologic fluids or gases are rarely without the influence of at least minimal pressure. This fact increases the challenge of device calibration. However, it can be predicted intuitively that there may be a measurable "zero" or baseline density that could be monitored by the device by selectively "capturing" venous system readings during the lowest point in the cycle (most likely during inspiration at end-diastole). It can also be predicted that there may be a mathematical relationship between peak and trough arterial and venous density and flow values and the baseline density value. This prediction allows for the potential determination of the baseline calibration density by means of extrapolation. Another means of device calibration, much less desirable because of its semi-invasive nature, would be the measurement of the density of an in vitro blood sample at atmospheric pressure.

The best method for ultrasound (US) or electromagnetic (EM) pulse delivery and detection must be determined. Potential devices would include conventional high frequency ceramic piezoelectric US transducers, RF (radio frequency) US transducers, polymer piezoelectric US transducers, IR (infrared) receivers, and Fiber Bragg Grating (FBG) Laser receivers, not excluding other existing and/or future transducers or sensors which are found to be applicable. All of these devices are referred to herein as "transducers" and/or "sensors." The frequency and amplitude chosen for the input signal, as well as the mechanism of its delivery, will depend upon requirements for patient safety and requirements for proper tissue penetration and conduction of the acoustic wave.

The device must be capable of detecting transit time shifts as low as 9.8 picoseconds in order for it to have resolution of 1 mmHg pressure, which would be ideal for medical purposes. Medical ultrasound typically operates in the frequency range of 1 to 10 MHz. This device will likely require a higher frequency acoustic input signal for accuracy. However, lower frequencies better penetrate tissues with less attenuation.

Input signal attenuation and penetration varies between tissue types and according to the frequency. For example, according to Dowsett, Kenny and Johnston: The Physics of Diagnostic Imaging, chapters 17, 18; attenuation coefficient/frequency (dBcm-1 Hz-1) are listed for the following tissue types: muscle: 1.8-3.3; fat: 0.6; brain: 0.9; blood: 0.2; bone: 20. These variations in signal attenuation can be exploited in order to enhance the quality of the output signal, since blood is a better conductor of acoustic energy and less prone to signal attenuation when compared to biologic tissues. However, signal attenuation is much higher at high frequencies. Nevertheless, there exists enough of a difference between its value in blood and tissues that the principle remains the same. Ideally, the chosen frequency would attenuate within the skin and subcutaneous tissue before directly reaching the receiver yet conduct effectively along the vessel to the receiver. This would greatly enhance the signal-to-noise ratio.

Signal input from the sender must consist of brief pulses or "clicks" generated at specific intervals (e.g., 10 to 100 times per second) in order to detect all phases of the pressure cycle. The brevity of the impulse will be important for precision and will guide the choice of acoustic energy to be considered for use in the device. There will likely be a need to focus the ultrasound beam in such a way as to effectively maximize the intravascular acoustic travel distance (the distance that the sound wave actually travels within the blood vessel on its path to the receiving transducer). Such focusing will probably take the form of a simple transducer array, possibly requiring the use of more than one frequency.

Also for the sake of precision, the operational goal of device 10 is for the sending transducer to create a focused shock wave "click," and to clock its transit time within the blood to the receiving transducer. Since sound waves travel in all directions from their point of origin, it would be difficult to know the exact length of the intravascular sound wave path. However, fixing the transducer separation by using rigid housing and using a technique such as Time-Reversal Mirrors should define the wave path well enough to accomplish the desired level of precision. Maximizing and closely defining the length of the sound wave path is a crucial step for the accurate determination of intravascular sound speed. Detection and timing of the first arrival wave would indicate the transit time for the most direct path between transducers. Since sound speed is higher in blood than in the surrounding tissues, then this first arrival wave would be considered to have passed through blood.

Figure 2:
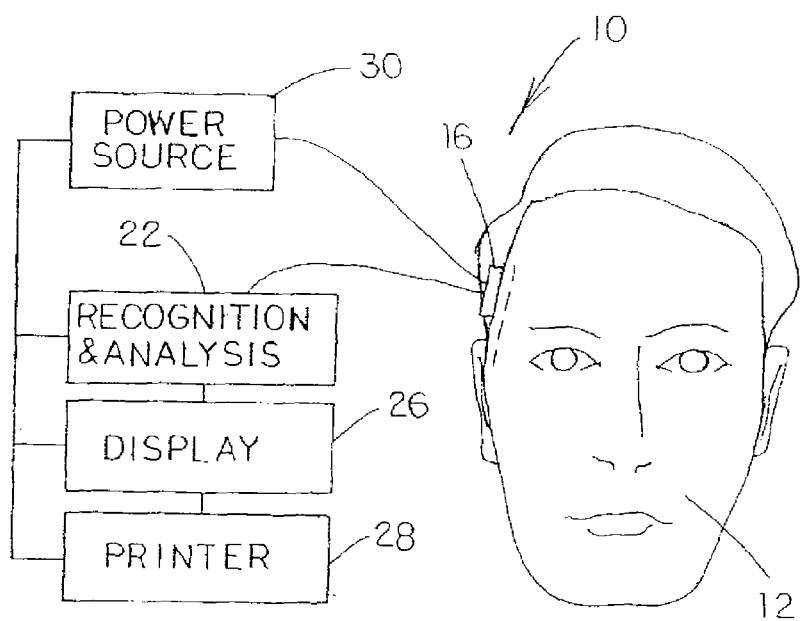
FIG. 2 is a view like FIG. 1 of another version of the new and improved noninvasive vital sign measurement device of the invention showing a single sender and receiver.

Referring to FIG. 2, there is shown the device 10 of the invention in a single transducer variant comprising a transducer 18 applied to the skin of a body part 12 using an acoustic conductive medium such as above described. The single transducer functions as the sender, generating the acoustic input signal and as the receiver, generating the output signal. The single transducer 18 could yield the same data as the two-transducer method, above described. This may be accomplished by measurement of the transit time (the echo) of the acoustic wave to and from the far side of the specific vessel as the wave reflects off the vessel wall interface. Using this method, the angle of the transducer axis to the vessel is critical. The transducer must remain as close to perpendicular as possible to the plane of the vessel in order to eliminate errors caused by blood flow. As this method may not be as precise as the two-transducer method, it may be more useful for trending.

Phase-shift detection could be used as another signal processing technique in both the single and two-transducer methods to detect transit time shifts in vessels, chambers, body cavities and compartments, or airways. Since the velocity of acoustic transmission changes with varying pressure, the phase of the reflected or transmitted wave would shift proportionately with changes in transit time and therefore would also shift with changes in pressure. When using this phase-shift detection technique during vascular system or static fluid compartment measurement, very high frequencies (most likely within the range of 50 MHz to 7.5 GHz, but not excluding higher or lower frequencies) would be required in order to ensure precision. When analyzing the pulmonary or pleural spaces, lower frequencies (probably ranging from 100 KHz to 1 MHz, but not excluding higher or lower frequencies) would be required.

Such a phase-shift detection technique would not truly utilize the Doppler-effect in its detection of phase shift. Since there is no flow involved within static compartments, then there is no Doppler-effect possible. Within vessels, however, the desire is to cancel out any effect of flow and motion artifact. Therefore, while phase-shift may still be a measurable quantity, the Doppler-effect would not be applicable in either the vascular setting or the static compartment setting.

The single transducer transit time and phase-shift detection methods may be more suitable for measurements of static compartments or hollow organs within which flow is not a significant factor. They may be less suitable for vascular pressure measurements where they cannot easily cancel out noise caused by flow.

IR, RF, and/or Laser technology may also be used in transducer design for the single or two-transducer methods. The arrangement of the sender and receiver transducers would be as in FIGS. 1 and 2. Sensor function could be enhanced with the use of Laser technology with Fiber Bragg Gratings (FBG's) tuned to a specific US frequency. FBG Laser may be especially useful in sensor design due to its capability of sensing high frequencies and its resistance to RF interference.

A third type of arrangement for the transducers utilizes three or more transducers, one sender and two receivers arranged in the order, receiver-sender-receiver, as they lay longitudinally over the vessel. Again, these transducers could be of piezoelectric design or could use any of the other advanced technology above described. The two receiving transducers would clock the US wave front as it passes upstream and downstream from the centrally located sending transducer. The velocity values would be summed in order to cancel out the effect of blood flow and to separate it from the effect produced by pressure fluctuations. Like the two-transducer technique, this technique—given very specific placement of the transducers and chosen frequencies—would also take advantage of the fact that the attenuation coefficients of biologic tissues differ from that of biologic fluids. However, accuracy would likely not be as precise as with the two-transducer method since the wave paths upstream and downstream do not cross the same section of vessel, and thus cancellation of turbulence-induced signal variations may not be as effective. See FIG. 3.

Figure 3:
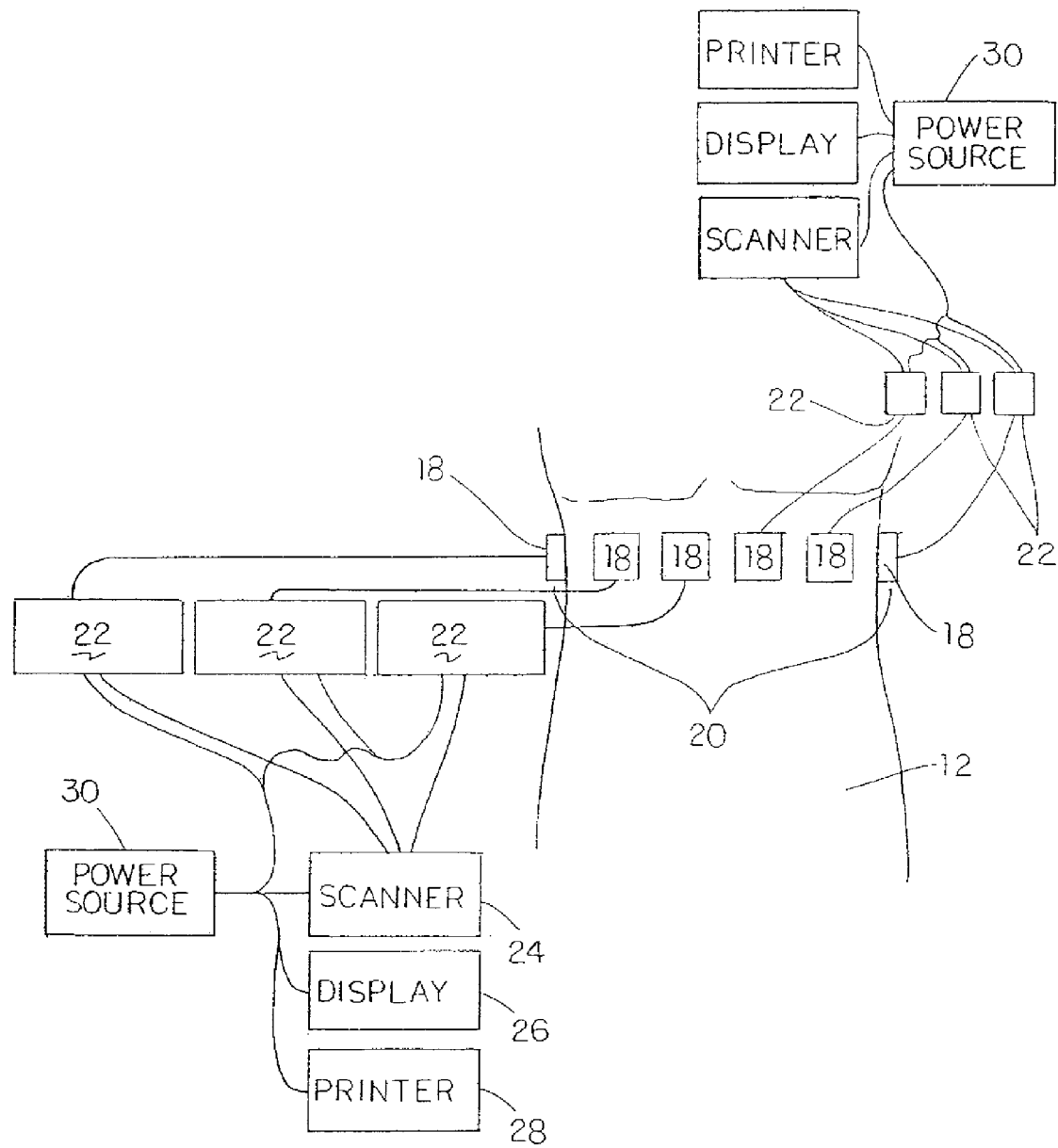
FIG. 3 is a view of another version of the new and improved vital sign measurement device using three or more transducers.

Each of the sensors 14, 16 and 18 and each of the monitoring devices 10 of the invention illustrated in FIGS. 1-3 are connected to a computer that is programmed with recognition and analysis software. Depending upon the function of the sensor 14, 16 or 18, i.e., whether the sensor is a sender, a receiver, or both, the computer software will differ as to each recognition and analysis computer 22 to receive the signal from its individual sensor 14, 16, 18 and convert the same into a measurement of arterial and venous blood densities and blood flow velocities, blood pressure, pulse rate, vascular resistance, cardiac output, pressure pulse wave velocity, and the like. The display will include both instantaneous measurements and a plot of each measurement versus time.

Scanners 24 are provided to scan each of the computers 22 sequentially from about 10 to about 100 times per second, depending upon the particular clinical application. Each of the scanners would be operatively connected to a display 26 that would display the data from each of the sensors 14, 16, 18 of each of the measurements, in the form of both instantaneous measurements and the historical trends of each measurement. The display would be combined with a selection switch by which each measurement and trend could be selectively displayed.

Attached to each display would be a printer 28 which would print out current vital signs and a continuous record of highest, lowest, and trends of each measurement, as well as trends for each patient and each location of a sensor 14, 16, 18.

Each of the sensors 14, 16, 18, each of the recognition and analysis computers 22, each of the scanners 24, each of the displays 26, and each of the printers 28 are connected to a power source 30.

In the single sensor device 10 illustrated in FIG. 2, the sensor 16 is connected to a single recognition and analysis computer 22 which is connected directly to a display 26 and to a printer 28.

Precise measurement of biologic fluid density is the critical step in ensuring accuracy by way of continuous calibration for the device using any of the above methods. Also, such continuous and precise monitoring of blood density would be extremely useful in the diagnosis and treatment of trauma patients and any other malady involving rapid or profound blood loss or physiologic fluid shifts. See device 100.

Morbid obesity would likely make this device unusable as it would increase signal attenuation and would therefore make readings very difficult. There would be a marked decrease in the signal-to-noise ratio in patients with thick layers of adipose tissue. When working within normal physiologic blood pressure ranges, period calibration of the device using a conventional sphygmomanometer would solve the problem of accuracy in most situations where body habitus interferes with the normal function of the device. However, in the non-obese patient, even in cases where calibration is not possible, such as a profound hypotension or cardiac arrest, accurate readings may be attainable with the device.

Another challenge would be the design of a stable transducer-to-skin interface acoustic conductive medium. The interface must remain fixed in position for a number of hours. It must be comfortable to the patient, and provide reliable ultrasound conduction.

In summary, the vascular application of the device would be capable of accurately and continuously measuring arterial and venous blood pressures, pulse rate, blood density, and blood flow velocity, and it would be capable of calculating peripheral vascular resistance. When the venous system and interstitial space are monitored, the state of hydration can be assessed. When applied to the chest, then pulmonary, central venous, pleural space and cardiac monitoring may also be possible. The device may have many other uses, including the measurement of compartment, ocular, intra-abdominal, intracranial, and specific organ pressures. In addition, the device could be mated to other more conventional equipment, e.g., measuring oximetry and temperature.

Device 100

Another version of the new and improved noninvasive blood density measurement device 100 is a simpler form of device 10 of the invention for the purpose of supplying in vivo blood density information for medical monitoring and research. The function of device 100 is the same as that of device 10, except that ultra-precision is not required. As with device 10, the goal with device 100 is the noninvasive in vivo measurement of blood density. However, it will not have the necessary precision to detect the minute density fluctuations which represent pulse pressure. Therefore the device requires somewhat less sophistication.

The primary goal of monitoring blood density is to detect fluid shifts within the body. Also, because hematocrit is the main contributor to the density of whole blood, then both device 10 and device 100 are continuous noninvasive hematocrit monitors. They could, therefore, both be used to monitor multiple parameters in critically ill or injured patients or be used to spot check patients for blood disorders.

Within the practice of nephrology, the monitoring of blood density during dialysis is well known to be important as it is used to predict and preempt sudden onset of hypotension. However, the relevance of blood density values and trends as they relate to the status of critically ill or injured and potentially unstable "critical" patients is not well known. Under the current state of the art in blood density measurement, comprehensive research on the clinical relevance of blood density is not possible. Device 100 is needed so that such clinical relevance, or lack thereof, can be discovered.

Currently the state of the art in blood density measurement is practiced using only extracorporal methods. One method uses frequent blood sampling and subsequent laboratory analysis. Another less precise method uses a continuous optical device during hemodialysis which clamps onto the dialysis tubing and measures the concentration of the extracorporal blood. Continuous blood density monitoring is currently unavailable for patients who are not undergoing hemodialysis. Frequent blood sampling, although precise, is labor intensive, expensive, and impractical. There is a need for a tool such as device 100 which measures blood density conveniently, continuously, noninvasively, and in vivo. In addition, device 100 may be capable of providing continuous data relating to arterial and venous blood flow velocities, extravascular fluid stores, and analogs of vascular resistance and cardiac output.

Figure 4:
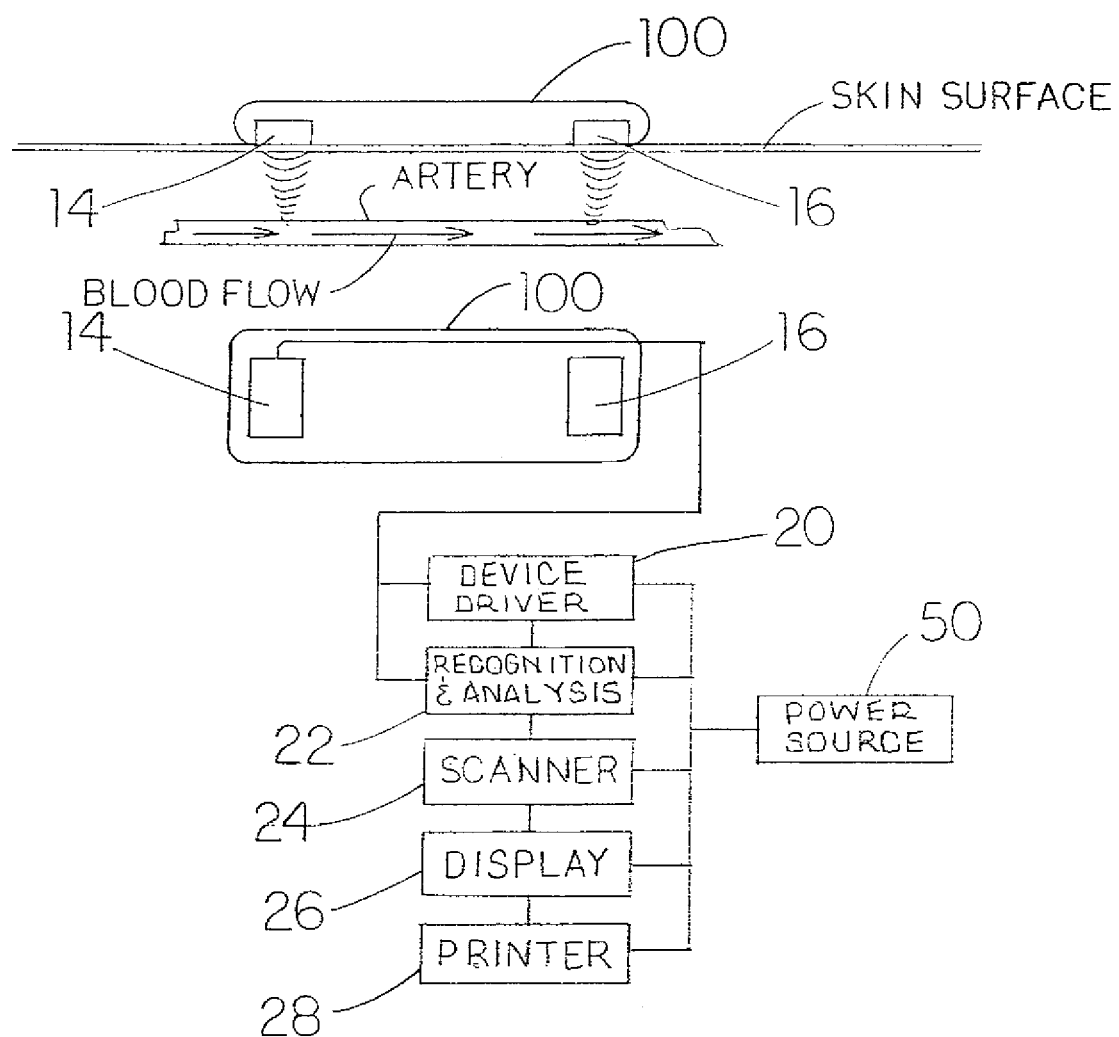
FIG. 4 is a view of still another version of the new and improved vital sign measurement device similar to that shown in FIG. 1.
Figure 5:
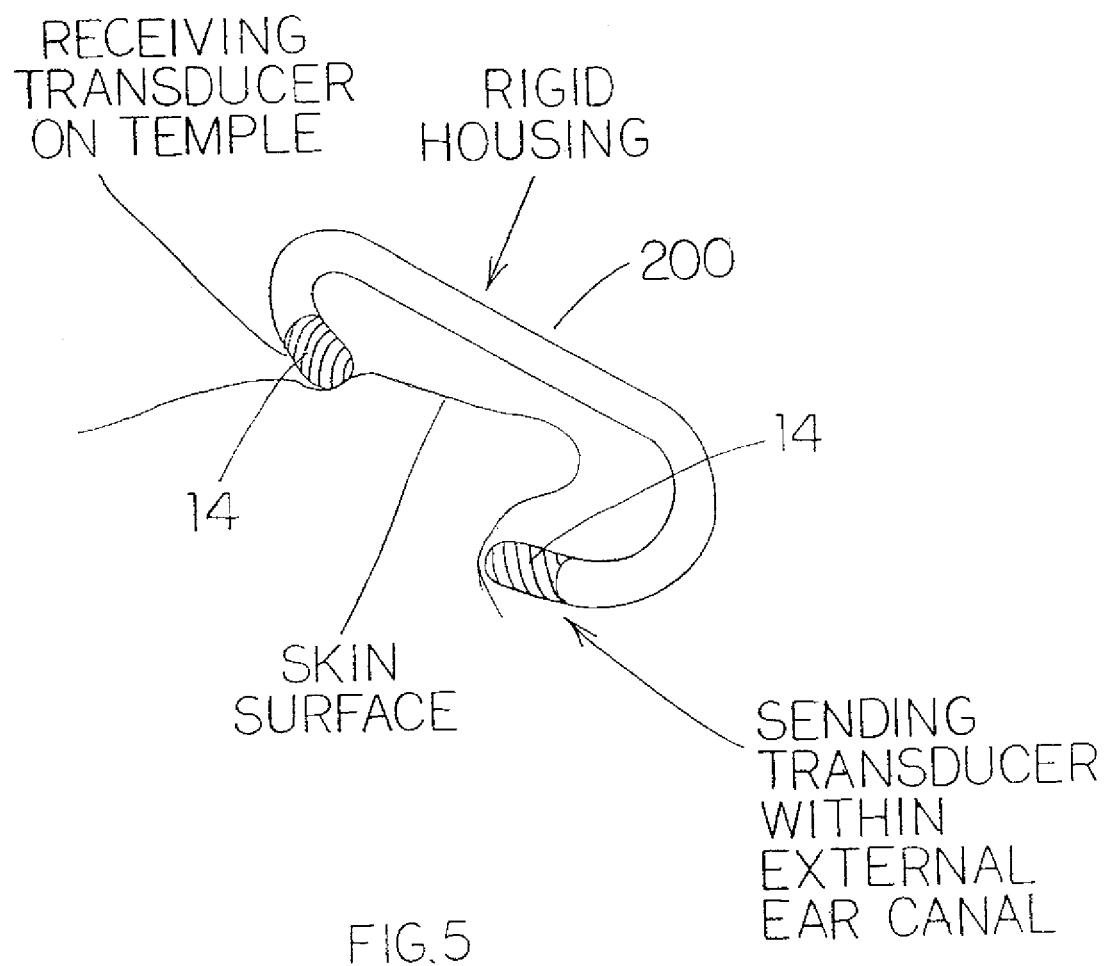
FIG. 5 is a view of still another version of the new and improved vital sign measurement device in which the transducers are mounted on opposite sides of a blood vessel or vessels.

This description of device 100 is also an addendum to the description of device 10. Most of the technical aspects of device 10 are identical to that of device 100, and therefore, the text of this description applies fully to that of device 10. FIGS. 4 and 5 illustrate one possible form of device 100 and device 10 of the invention. Although the basic function of the two devices is almost identical, the goals of precision and clinical application differ and would dictate certain technical variations.

Physiological Basis for Measurement of Blood Density in Critical Patients

During severe physiological stresses there are significant alterations in blood density as the blood becomes more concentrated or more dilute. These alterations occur as a result of transcompartmental fluid shifts that, in turn, are caused by physiologic compensations in for form of osmotic or hydrostatic effects. Significant fluid shifts—and thus dynamic changes in blood density—occur during shock from any cause including hemorrhage, sepsis, spinal cord injury, toxins, and cardiogenic causes. Less significant, but still noteworthy, are fluid shifts and blood density changes that occur during more ordinary clinical situations such as orthostasis (1), dehydration and rehydration, various pharmacological therapies, and weightlessness. Therefore, the measurement of blood density and its trends may thus become an important tool for ruling out certain causes of syncope and dizziness.

When the condition of low intravascular volume or pressure occurs, physiologic compensations are triggered in an attempt to maintain blood volume and thereby blood flow to the vital organs. Under these conditions the vascular system osmotically draws fluid into the blood from the extravascular space. This results in dilution of the blood and a drop in blood density (hemodilution). For example, hemorrhage results in rapid fluid movement from the extravascular to the intravascular space and thereby causes hemodilution. (2) The vascular system is, in effect, "borrowing" fluid from the tissues in order to preserve blood volume and flow.

Similarly, an infusion of IV fluids will initially cause hemodilution and a drop in blood density. However, the dilution from IV fluids will not persist if the blood volume and osmotic and hydrostatic pressures remain adequate, because the fluid will eventually migrate from the blood to the extravascular space (if it is not first lost through renal excretion or other insensible losses). The vascular system thus gives back fluid that it may have once "borrowed" from the tissues, and the blood density or concentration will drift back toward a more normal range.

Certain catastrophic vascular effects are triggered by prolonged or severe shock, sepsis, burns, crush injuries, and toxins. The result of these effects is capillary damage and leak. This leaking causes fluid to shift from the blood to the extravascular space, and thus results in a blood volume decrease accompanied by a blood density increase (hemoconcentration). Since diuretics and blood transfusions effectively cause hemoconcentration, and IV fluids cause hemodilution, then device 100 could also become a useful tool in the monitoring and management these types of therapeutic interventions.

The clinical course for severely ill or injured patients is typically very dynamic. As the disease process takes its course, the physician then responds with aggressive treatment using surgical techniques, vasoactive drugs, IV fluids, and blood products. Multiple events take place in rapid sequence, and each has its own effect upon blood density. In such dynamic situations, the interpretation of blood density values and trends would be complex. Clinical studies must be done in order to define the parameters for use of device 100.

Since blood density is already known to be an important indictor to observe during hemodialysis, it is reasonable to assume that there is also a relationship between the clinical course experienced by the critical patient and the magnitude and rapidity of the changes in blood density. It is likewise reasonable to assume that there are physiological limits to blood density and that high and low extremes are not compatible with life. Therefore, blood density monitoring may be as important in the management of any critical patient as it is in the management of a hemodialysis patient.

The density of blood is determined by multiple factors, the most influential of which are the hematocrit and serum protein level. Other determining factors are pressure, temperatures, and dissolved sugars, salts, and gases. Since device 100 is not designed for ultra-precision as is device 10, the blood pressure contribution to density values will be negligible. For purposes of simplicity during earthbound research, pressure would be assumed to be fixed at one atmosphere. Also, since it has a significant effect upon density, a calibration or correction for temperature must be accomplished.

The device would be useful in any medical setting where care is provided for critical patients. This would include such settings as emergency departments, intensive care units, surgical or post-operative areas, burn units, hemodialysis units, military mash units, and battlefield settings. It would also be useful in aerospace research settings. There are significant transcompartmental fluid shifts that occur in the zero gravity environment. (3, 4)

In order to ultimately find its niche among the tools of clinical medicine, the device must initially serve the purpose of research tool. To date it appears that there has been very little research done and in the area of blood density and its correlation to the clinical status of critical patients. However, the few studies that have surfaced do seem to indicate that such monitoring would probably be useful, provided that convenient method of measurement is available. There is currently no existing device for monitoring blood density in vivo and noninvasively on a continuous basis.

Device Function—Another Version

The function of device 100 depends upon in vivo sound speed measurement within blood. Its basic function is identical to that of device 10, but with less required precision. Acoustic transit time (time-of-flight) is measured using the "pitch-catch" method between proximal and distal transducers in both upstream and downstream directions simultaneously. Another option would to replace one transducer with a reflector. The remaining transducer would act as both sender and receiver, and would clock total time-of-flight. Either device would be applied to the body wherever the best arterial and venous signal can be obtained. These time-of-flight measurements would be then be used to calculate acoustic velocities upstream and downstream. Readings would be taken from both arterial and venous blood and then the data from each or averaged data from both would be fed into a microprocessor where it would be converted to blood density and flow values.

When using the time-of-flight method to obtain blood density readings, the effect of blood flow velocity upon time-of-flight must be negated. Although the condition of "static" blood is not possible under most in vivo circumstances, a correction can be made for the effect of flow upon the measurements. BY using the upstream and downstream velocity values, a calculated "static equivalent" acoustic velocity can be obtained. The effect of flow is thus cancelled out mathematically by dividing the sum of the upstream and downstream acoustic velocities by two. The result is the acoustic velocity equivalent as if it were measured within static blood.

In practical terms it may be very difficult to separate the arterial and venous signals since, in the circulatory system; the arteries and veins are usually paired and located in close proximity to one another. The signal would thus be essentially already averaged along with the portion of the signal attributable to capillary blood.

Based upon the UNESCO equation for sound speed in water, this resulting "static equivalent" acoustic velocity value has a direct mathematical correlation with blood density as discussed in the description of device 10. The UNESCO equation—which was developed for the study of sound speed in seawater—can be used to substantiate this method, since blood, like seawater, is simply water with certain substances in solution or suspension.

Blood flow velocity would be calculated by subtracting the upstream from the downstream acoustic velocity and dividing by 2. Both venous and arterial flow velocities can be calculated in this fashion. This time-of-flight method of blood flow velocity determination differs from that of the Doppler method, since its operation depends upon sound-speed measurements and not phase-shift data.

Since the device senses blood flow in both directions, it would be able to differentiate venous from arterial flow. In terms of practical function, the fact that it is sensing blood flow assures that the device is indeed reading the density within intravascular fluid and not within extravascular fluid.

Interestingly, device 100 may also be capable of providing a measurement of acoustic velocity within the extravascular space. This would be useful in monitoring the body's stores of extravascular fluid, i.e., hydration status. Sound speed should change proportionately with the fluid "saturation" of the extravascular tissue.

Another method of assessing the dynamic status of the extravascular fluid would be to monitor the difference between arterial and venous blood density values. This may present a challenge if the arterial venous blood density measurements can not be distinguished one from the other, but the data obtained from this method would contain relevant information relating to the movement of fluid into and out of the extravascular space. For example, when the arterial blood density is found to be higher than the venous blood density, the conclusion might be made that physiologic compensation is underway and that fluid is moving from the extravascular space into the blood, such as might be seen during blood loss. This differential arterial-venous blood density value would probably be detectable prior to any significant alteration in whole blood density and would serve as a very sensitive and contemporaneous real time gauge of intravascular-extravascular fluid movement.

By applying existing state of the art methods of measure, this device could also sense pulse-wave velocity by clocking the pulse-wave as it passes by the two transducers. Pulse-wave velocity is the speed of the arterial pressure wave as it propagates from the heart to the peripheral tissues. It can be used to estimate cardiac output when adjusted for patient age. An analog of cardiac output could most likely be calculated from mean arterial blood flow and pulse-wave velocity. An analog of vascular resistance could also theoretically be calculated if mean arterial and venous pressures and blood flow are known. The actual analog values of cardiac output and vascular resistance obtained in this manner would be useful only for trending. (5)

Another already existing method of measuring pulse-wave velocity involves mating the device with an electrocardiogram (EKG) electrode and measuring the time from the QRS impulse to the arrival of the pulse-wave at the device. Also, contour analysis of the pulse pressure wave is a method currently being used to estimate cardiac output. These methods seem to be gaining some validity within the research literature as being reliable for trend monitoring of cardiac output. (6)

Like device 10, device 100 would digitally display the instantaneous arterial and venous blood density and blood flow velocities, the analogs of cardiac output and vascular resistance, and their trend lines as well as rate of change.

The acoustic frequency range to be used would vary with the desired separation distance between transducers. Both are yet to be determined. As with device 10, the electronics required would include a device driver 20 that controls each transducer by triggering impulses at a rate between 10 Hz and 100 Hz. Each transducer would act as both sender and receiver and would be connected to a signal processing computers 22 that would note time-of-flight for each impulse and then calculate the dimensions and location of the vessels and arterial and venous blood density and flow velocities. The receivers would also send pulse-wave velocity data to the computers 22 for signal processing and calculation of vascular resistance and cardiac output analogs. Scanners 24 would collect data from the computers and transmit it to the display 26 and printer 28. A power source 50 would be connected to all components.

The housing for the transducers (FIG. 4), which would most likely be constructed from medical grade epoxy or silastic, would fix the distance between the two transducers and set the proper angle to the skin in order to create the most optimal signal for processing. The requirements for housing style might differ depending upon the anatomic location to be monitored. For use on the arm, for example, the housing must be as flat as is practical and secured in some fashion. Testing must yet be performed in order to find the most optimal transducer separation, angle, and frequencies, as well as the best type of acoustic conductive medium, arm band style, etc.

There would possibly be a need to tune (power, transducer wavelength, transducer triggering frequency, and beam spread or scatter) the ultrasound beam in such a way as to effectively maximize the intravascular acoustic travel distance (the distance that the sound wave actually travels within the blood vessel on its path to the receiving transducer). Such tuning might take the form of a transducer array possibly requiring the use of more than one frequency.

As with device 10, and for the sake of precision, the operational goal of device 100 is for the sending transducer to create a shock wave "click," and to clock its transit time within the blood to the receiving transducer. Since sound waves travel in all directions from their point of origin, it would be difficult to know the exact length of the intravascular sound wave path. However, fixing the transducer separation by using rigid housing and using a technique such as Time-Reversal Mirrors should define the wave path well enough to accomplish the desired level of precision. Maximizing and closely defining the length of the sound wave path would be a crucial step for the accurate determination of intravascular sound speed. Detection and timing of the first arrival wave would indicate the transit time for the most direct path between transducers. Since sound speed is higher in blood than in the surrounding tissues, then this first arrival wave would be considered to have passed through blood.

Therefore, both sending and receiving transducers may need to be tuned (focused or defocused) to maximize the path within the blood. Tuning may need to be individualized for each patient and for each anatomic location. The induced intravascular "click" would emanate in all directions from its point of origin within the vessel. Much of the resulting wave energy would then travel through the blood (arteries, veins, and capillaries) and be detected by the receiving transducer. The effect of this tuned shock-wave technique would be to maximize the intravascular travel distance of the acoustic wave. It would also improve signal-to-noise ratio for the time-of-flight impulse.

The remainder of the wave energy would reflect and/or scatter and would ultimately also be detected by the receivers. The data collected from the reflections would reveal the status of the extravascular fluid balance, and would also be used to determine the size and location and the selected vessel. This data would in turn be fed into the signal processors and could be used to guide the tuning of the ultrasound beam. By applying signal processing techniques, the true intravascular signal would be separated from the signals resulting from reflections and scatter.

For device 10 this technique of tuned input and detection would likewise be applied for the purpose of signal enhancement and precision, even though input frequencies and transducer types might differ.

The type of transducer to be used in device 100 is also yet to be determined. Common piezoceramic transducers may work well, but in order to assure the proper brevity of the input impulse "click", other types of transducers may be required, including but not limited to, polymer, piezo, laser, infrared, radio frequency, Fiber-Bragg laser receivers, and hybrid transducers.

Device Function—Still Another Version of Device 100

Although sound velocity measurements would ideally be made longitudinally through a vessel, in practical terms this might be very difficult to do non-invasively. Sound waves prefer to travel along straight paths. Therefore the most practical body location chosen may involve the acoustic wave crossing a vessel perpendicularly. If high enough frequencies are used (1 to 20 MHz), then the desired precision might still be accomplished. The vessels adjacent to the external ear may be amendable to such a monitoring method. Other locations such as the perioral and post-auricular arteries might also be used.

A specific example is the superficial temporal vessels, located just anterior to the tragus of the external ear. In this case the vessel may be monitored by placing the sending transducer against the anterior wall of the external ear canal just behind the tragus. The receiving transducer would then be placed against the skin anterior and superior to the tragus, positioning the vessel between the two transducers. The sender would emit its impulse directly towards the receiver across the vessel. Continuous time-of-flight measurements would be continuously corrected for temperature changes and converted into blood density values. If the separation between transducers can be maximized, and if frequencies used are high enough (500 KHz to 100 MHz), then desired precision might be accomplished. See FIG. 5. Temperature correction may be accomplished by incorporating a temperature probe into the device just adjacent to the transducer or with the use of a dual-mode oscillator crystal, which has the characteristic of self-temperature-sensing.

In order to maintain accuracy of sound velocity readings and thus blood density measurements, the device would incorporate a temperature probe and also electronics for continuously monitoring the mechanical separation between transducers. Since movements such as chewing and talking may change the separation of the transducers, the device could instantaneously adjust for the change and recalculate sound speed based upon the new distance. In all practicality, the separation between the transducers or transducer and reflector should be fixed by using a rigid housing or include a monitoring mechanism for measuring changes in the separation distance between the transducers or reflector. This would apply to both device 10 and device 100. Also, with either device, it may be relatively easy to incorporate an oximeter. The application of a small array at the receiver may provide vessel diameter information and thus an analog of pulse pressure.

In summary, device 100 may provide the following continuous data from a stable platform overlying a vessel near the ear: [0109] 1. Blood density [0110] 2. Temperature [0111] 3. Oximetry [0112] 4. Pulse rate [0113] 5. Pulse pressure analog Another device 120 of the invention is an intravascular catheter that contains sensors for in situ measurements of multiple whole blood physiologic and hemodynamic parameters. It would be a unique and useful diagnostic tool that would facilitate rapid decision-making and optimization of medical management and resuscitation of patients suffering from the most challenging and life-threatening medical conditions. The instantaneous monitoring by the application of the invention would provide a means by which to immediately assess the effectiveness of fluid and blood administration as well as pharmaceutical or surgical interventions. Currently there exists a significant lag-time between the initial recognition of a problem, such as sudden hypotension, and the obtaining of lab results that may or may not confirm clinical suspicions of the problem cause(s).

The physiologic and hemodynamic data obtained with the use of device 120 would allow the clinician to more quickly differentiate the causes of hypotension from any cause or combination of causes. Intravascular monitoring would provide information useful in determining the cause of shock, e.g., sepsis, blood loss, and autonomic malfunction such as that caused by spinal cord injury. For the clinician, knowing the level of vascular resistance and vascular fullness would also improve the ability not only to differentiate the causes of abnormal vital signs, but also to determine the best course of treatment in each circumstance. Such treatment may include infusion of saline, blood, both saline and blood, or pressor medications; the performance of specific surgical inventions, appropriate airway management, or fracture stabilization; or, in some cases, simply the administration of pain medications. Continuous monitoring of this broad range of physiologic and hemodynamic parameters would also provide immediate feedback on the effectiveness of the above interventions.

Primarily, the device is intended for peripheral vascular (venous or arterial) use in prehospital, emergency, surgical, post-surgical, burn unit, and ICU environments. The invention may be useful in any other medical patient or research environment where it might be desirable to measure and/or trend the above stated physiologic and hemodynamic values. These include but are not limited to military, aerospace, and subsurface marine environments. Other clinical or research applications may include the trending of any biologic fluid within any body space, whether it be peripheral or central vascular or fluid filled body cavity. Examples of confined body cavities would include the urinary bladder, gallbladder, intra-abdominal, brain ventricles or spinal fluid. The device could possibly be used to monitor the status of the above parameters within extremity fascial compartments or post-op plastic surgery skin flaps. It may be especially useful to also monitor pH or lactic acid level within a compartment where there is potential muscle necrosis to determine the need for and improve the timeliness of rapid surgical intervention. In addition to vascular or compartment pressure readings, the catheter could potentially be used to measure the pressure in gas-filled structures such as pulmonary airways and bowel lumen. It would be useful in the clinician's office for routine on-the-spot laboratory analysis.

When the catheter device is placed intraarterially, systolic, diastolic and mean blood pressures, pulse pressure, pulse rate, and the incorporated physiologic parameters would be displayed continuously. This type of information is routinely used in evaluating critical care patients. In addition, local blood flow velocity and calculated local vascular resistance (LVR) would also be displayed continuously. Ideally the clinician would want to know the level of total systemic vascular resistance (SVR) which relates to total sympathetic vascular tone. But SVR cannot be obtained from a peripheral catheter. SVR, which is commonly calculated in physiology research, is an important factor in determining the workload of the heart and how the vascular system is acclimating to various insults, such as trauma or infection. Although one cannot determine cardiac workload from LVR, it is theorized that LVR trends would parallel SVR and therefore be useful for observing changes in cardiac workload and sympathetic tone. LVR cannot be measured by any blood test and is not currently being measured for critical care resuscitation purposes in any clinical realm.

Since blood density is being precisely monitored, vascular volume can be determined by injecting a small volume of IV fluid (saline) and observing the change in blood density. Vascular volume is then calculated by the common dilution formula, BV=Vi*.rho.1/.DELTA.rho., where BV is blood volume, Vi is the volume of saline injected, .rho. is blood density and DELTA.rho. is the change in blood density observed as a result of the given fluid injection. Cardiac output can therefore also be calculated by the formula CO=BV/T, where CO is cardiac output, BV is the above calculated blood volume, and T is the time that it takes for the change in blood density to occur after administering a given volume of saline (the time that it takes for the heart to circulate the saline throughout the vascular system one time). Previously, information about vascular tone, vascular volume, and cardiac output has been confined to the realm of medical research and unavailable for routine use in clinical medicine.

Venous monitoring with the present invention would yield the same valuable blood density data as with arterial monitoring. Device 120 would also supply venous physiologic and hemodynamic parameters. In some circumstances, it may be valuable to perform trending of venous physiologic data and hemodynamic data. Venous placement of the catheter would not require special expertise and could be initiated by paramedics in the prehospital environment. Like the arterial catheter, the venous catheter would yield useful data continuously.

Standard arterial pressure monitors, because of the hydraulic transducer, can be clumsy due to the tubing and pressure bag. They require time consuming calibration. They do not provide information on blood concentration, blood flow velocity, temperature, blood gases, pH, oximetry or lactic acid level. Device 120's pressure sensor could be quickly calibrated to atmospheric pressure prior to insertion and thereafter would continuously self-calibrate for temperature changes. It would not require calibration for blood concentration or blood flow readings.

A. Blood Concentration and Hematocrit Measurement by Acoustic Methods

It is known that sound speed in whole blood is determined by total protein concentration[11], the concentration of ions, and the temperature[12]. The majority of protein in whole blood resides within the hemoglobin of the red blood cells (RBC's)[10, 11]. Therefore, not only can sound speed be used to very precisely measure blood density, it can also be used to measure the relative number and hemoglobin content of the RBC's.

The function of the device 120's blood concentration monitor depends upon the measurement of several properties of whole blood acoustic propagation. These include ultrasound velocity, attenuation, and backscatter measurements.

1) Ultrasound Velocity: By measuring high frequency sound wave time-of-flight, velocity can be calculated very precisely[9]. Therefore, sound velocity in whole blood can be used to accurately measure and trend blood density[11, 12]

The speed of sound in any liquid is also influenced by temperature[13, 16]. Therefore, if blood density is to be measured by the sound-speed technique, then it is imperative that temperature be taken into account. The primary determining factors for blood density are the total blood protein content and salinity. Within the human physiologic range, however, changes in salinity do not significantly affect sound speed[11, 13].

Whole blood consists of particles (cells, platelets, and insoluble plasma proteins) suspended within a water solution containing primarily salt ions, sugar molecules, and soluble proteins. The particles in suspension do not necessarily possess the same density as the solution itself. Therefore, the velocity of sound across a sample of whole blood is determined by the sum of the velocities of the blood components within the path of the sound wave[11]

Most blood protein resides within the red blood cells in the form of the iron containing protein hemoglobin. As a result, changes in sound velocity are directly proportional to changes in the concentration of hemoglobin within the sound wave path[10, 11] Velocity measurement is, therefore, an acceptable method of total hemoglobin estimation[7, 11, 12] Since the hemoglobin (Hgb) resides within the red blood cells (RBC's), then sound speed is also proportional to hematocrit (Hct), the percentage of whole blood consisting of RBC's[10] For the purposes of the design of device 120, Hgb and Hct are so closely linked in terms of their relationship to sound speed that they will be considered one and the same and will be referred to heretofore as H/H.

When serum protein levels are unusually high or low, however, an error in H/H estimation may be produced in the sound speed method sup.11 For example, a high serum protein level would result in overestimation of H/H, and a low serum protein level would result in underestimation of H/H. Nevertheless, methods exist for very precise measurement of sound speed[9] and, within the normal human range of H/H[11], sound speed has high overall correlation to H/H. In the very low H/H range, however, anomalies in serum protein level produce proportionately larger errors in H/H measurement by the sound speed method. Therefore, in order to create a device that is accurate in all H/H ranges, it would be desirable to primarily use sound speed for H/H measurement and, to correct the results obtained in the lower range of H/H.

Others have shown that sound speed[11], sound attenuation[15], and backscatter amplitude[14, 15] each have their own individual relationship to H/H within certain ranges of H/H. Because each individual parameter seems to possess a different level of accuracy within different ranges of H/H, it can be theorized that each parameter might be used to correct the measurement results of the other parameters. In the work for the above referenced patent, averaging of the parameters was used to achieve modest improvement in the accuracy of H/H measurement. It is an object of the current invention to enhance device accuracy by developing specific mathematical algorithms that better describe the influence of each parameter upon the instrument's accuracy.

2) The Relationship Between the Accuracy of the Sound Speed Measurement of H/H and the Serum Protein Content:

An in vitro study of random anonymous whole blood samples (n=30) to determine the correlation of hematocrit with sound speed, correlation was found to be high (R=0.93) in the overall population. Best fit was performed in this population of whole blood samples, and it was found by regression analysis that the relationship between sound speed c and Hct can be described as follows: Hct=1.0135(c−1520)+8.8874 By further regression analysis (R=0.85), it was found that the percent of error in Hct measurement produced by variations in serum protein level (SP) can be described by the following equation: % error=−30.354 Ln*(HCT/SP)+47.47

3) Continuous Precision Sound Speed Measurement:

The intravascular device would continuously measure acoustic transit times in order to calculate sound speed in whole blood, and thereby measure whole blood density. By continuously measuring transit times and minute shifts in transit times in rapid sequence (10 to 1000 Hz), such measurements, if made with precision, would result in accurate, reliable, and continuous blood density and H/H data. FIG. 1 illustrates the sound speed sensor as a single transducer-reflector pair with the reflector fixed at a specific distance, e.g., 5 mm. The transducer acts as both sender and receiver and is connected to a power source, recognition and analysis hardware and software, display, and printer.

The particular hardware that runs the sound speed sensor will depend upon available high fidelity equipment. An example of available equipment is that developed by Dr. Craig Hartley PhD, which is capable of detecting transit time of an ultrasound wave by detection of 1.degree. of phase change.sup.9. Using a 20 MHz ultrasound frequency, the method has been shown to be capable of detecting a 139 psec increment change in the time of sound wave arrival. Assuming average sound velocity in the human body to be 1540 m/s, the time increment of 139 psec time increment translates to a velocity increment of 0.0329 m/s between fixed transducers. From the above referenced NPC in vitro study, it was discovered that a sound velocity increment of 0.0329 m/s translates into a hematocrit increment of 0.0333%. This level of precision would be excessive for the purposes of blood density measurement. However, such precision could potentially be used in making pressure measurements (see the below description of a novel method of pressure measurement). Sound speed changes that occur as a result of pressure changes are extremely minute, and would not alter measurements done for the purpose of hematocrit monitoring.

Temperature has a significant effect upon sound speed in liquid.sup.13. Device 120 will include a probe which will allow for continuous calibration for temperature changes. A change in temperature of 1 degree. Celsius produces an error of 7.5 nanoseconds in time-of-flight across a sound wave path 10 millimeters in length. Therefore the conceptualized multiparameter catheter must have appropriate temperature compensation. This will most likely take the form of an off-the-shelf precision temperature probe embedded in the catheter tip, such as a thermistor or other miniature sensor. An alternative and unique method of precision temperature measurement utilizes an ultrasound technique called Dual-mode Oscillation. The actual method used will depend upon its ease of incorporation into the catheter and its accuracy and precision. Measurement of the temperature to within .+−.0.1 . degree. Celsius would probably be adequate for purposes of measuring H/H. It would provide a resolution of .+−.0.28% in hematocrit determination.

4) Attenuation: Whole blood protein, whether contained within cells or suspended in the plasma, absorbs sound. Therefore, as a sound wave travels through a sample of whole blood, the amplitude of the wave attenuates over a given distance depending upon the quantity of protein through which it passes. Most blood protein resides within the hemoglobin molecule. Cell membranes also have significant effect upon attenuation because of their sound absorption and sound wave scattering effect.sup.15. Device accuracy for Hct estimation, therefore, may be enhanced by the mathematical incorporation of attenuation values. This can be accomplished by measuring the amplitude of the received wave at the sound speed measurement transducer.

5) Doppler signal backscatter measurement. A significant proportion of ultrasound wave energy reflects off of cell membranes. The Doppler method applies this physical characteristic of sound to detect movement (flow) of whole blood within vessels, utilizing a change in pitch of the sound reflected off of the cells. When the cells are struck by the sound wave, they reflect and scatter the sound. The amplitude of the reflected Doppler signal is related to the number of cells within the sound field that have reflected the sound waves back to the transducer. Although the Doppler backscatter method may not be as amenable to precision measurement as sound speed, the backscatter coefficient (BSC) may be more representative of the actual number of cells present within the sound path at low Hct levels of <10%.sup.14. Interestingly, it is at such very low Hct levels that sound speed is least accurate. Therefore, measurement of backscatter level may provide a way to mathematically correct for inherent sound speed method errors in H/H estimation that occur secondary to anomalous serum protein levels when hematocrit is <10%. This can be accomplished using the same transducer as for sound speed measurement.

B. Arterial Blood Pressure Measurement

The parameters of systolic, diastolic, and mean blood pressure (and also venous pressure) could be incorporated into device 120 using several methods. Two existing technologies that could easily be incorporated into the catheter are:

1) The most common method currently employed in clinical practice, the traditional hydraulic pressure line with ex-vivo transducer, could easily be used because the catheter will be designed with a port. In this case no special adaptations would have to be made to the catheter.

2) A second type of intravascular pressure monitor involves a miniature solid state transducer within the tip of the catheter. This type of sensor is used for cardiac catheterizations and vascular research. The intravascular transducer would have the advantage of compactness with no need for the cumbersome hydraulic line and ex-vivo transducer. It could be calibrated prior to insertion. The disadvantage of the intravascular pressure transducer is the fact that position (if it is above or below the level of the heart) will affect the accuracy of the readings. But if the patient remains supine, however, the effect is minimal, producing only about a 2 mmHg change in pressure for every inch of elevation change. Position would not change pulse pressure readings.

3) Two novel methods for blood pressure measurement by sound speed method are:

a) As discussed above in the section on blood density measurement, a novel method for pulse pressure measurement involves precise continuous sound speed measurement. Theoretically, if changes in sound speed could be made with extreme precision (within incremental resolution of less than 2-4 picoseconds), then pulse pressure could be monitored. Due to calibration issues, systolic and diastolic pressures could probably not be measured. According to the UNESCO equation for sound speed in sea water.sup.13, there are minute changes in sound speed due to pressure changes. The advantage to using this method is that the data could be obtained using the same sound speed detection transducer(s) used for H/H measurement. A disadvantage to this method is the difficulty in obtaining the required picoseconds precision. Even if such precision could be obtained, it would be a very difficult matter to achieve accurate systolic and diastolic pressure measurements with this technique because of the fact that calibration to zero would be very difficult since the base-line would drift with changes in hematocrit, temperature, salinity, and changes in the elevation of the catheter-tip versus the level of the heart.

The UNESCO equation describes the relationship between acoustic wave velocity and pressure in water. The equation also takes into account other factors that contribute to alterations in sound speed, such as the salinity and the temperature. Although fluids (blood included) are considered incompressible, the equation shows that there should be minute but measurable changes in velocity associated with changes in pressure, even within the human blood pressure range of 0 to 300 mmHg.

To form theoretical support for the sound speed method of pulse pressure measurement, the space between two hypothetical transducers was assumed to be 2 cm (or 1 cm. between one transducer and a reflector). The UNESCO equation was then used to calculate acoustic velocity at pressure increments of 1 mmHg assuming constant fluid temperature at 37.degree. Celsius, constant salinity at 9 ppm, and variable pressure is expressed in kPa. Calculations using the formula V=D/T indicate that, in order for the device to have precision to within 1 mmHg, it must be capable of detecting shifts in transit time of roughly 2-4 picoseconds. Trending of the pressure within .+−.5 mmHg could be achieved by the detection of shifts of approximately 20 picoseconds across a sound path of 2 cm.

The method can be accomplished using either two transducers or one transducer with a reflector. When using two transducers, one must account for blood flow velocity (which ranges from approximately 0.2-1.0 m/s) and its effect upon time-of-flight between the transducers. The preferable method, therefore, would be to utilize a single transducer-reflector pair. This method would have the advantage of automatically eliminating the effect of flow and of doubling the length of the flight path (and thus doubling precision) without increasing the length of catheter.

According to the UNESCO equation, there is a 19.68 picoseconds change in the transit time across a 2 centimeter distance for every 10-mmHg change in pressure. The variability of the above mentioned physiologic values, however, may result in a much larger drift in transit times of several hundred nanoseconds of. According to the UNESCO equation, when salinity is fixed at 9 ppm, a change in body temperature of 1 degree Celsius would alter transit time by about 15 nanoseconds (a scale that is roughly three magnitudes greater than transit time shifts resulting from incremental changes in pressure). Similarly, with temperature fixed at 37.degree. Celsius, alterations in salinity of only 0.1 ppm would result in a change in transit time of about 0.85 nanoseconds. These values were calculated using velocity data obtained from the UNESCO equation at the National Physical Laboratories (NPL) interactive website.sup.16 and using the previously noted common equation, V=D/T. Such large-scale changes in blood density would of course occur over a period of minutes to hours and not milliseconds and therefore would not affect momentary pulse-pressure readings.

The best method for ultrasound (US) pulse delivery and detection must be determined. Potential devices would include conventional high frequency ceramic piezoelectric US transducers, RF (radio frequency) and Laser Optical-acoustic US transducers, polymer piezoelectric US transducers, IR (infrared) receivers, and Fiber Bragg Grating (FBG) Laser receivers, not excluding other existing and/or future transducers or sensors which are found to be applicable. All of these devices are referred to herein as "transducers" and/or "sensors." The frequency and amplitude chosen for the input signal, as well as the mechanism of its delivery, will depend upon requirements for patient safety and requirements to achieve proper blood penetration and conduction of the acoustic wave.

This device will likely require a frequency greater than 20 MHz for precision. In reality the attenuation of the signal at the higher frequencies may prohibit achievement of the desired level of resolution. Calculations using the UNESCO equation show that, even at a frequency of 100 MHz and a 2 cm transducer separation, the best resolution that can be achieved using current technology is only .+−.15 mmHg. At frequencies higher than 100 MHz, attenuation would most likely prevent practical transducer/reflector separation of more than a centimeter. However, at 20 Mhz frequency, resolution would be more than adequate for trending of blood density and blood flow. Future technologies could potentially arise that would make this method usable for systolic and diastolic blood pressure measurement, and not just for pulse pressure measurement.

Time-of-flight measurement would be made by the most precise method available. This could include such instrumentation as is available for standard sonomicrometry equipment. Phase-shift detection could be the most optimal signal processing technique because of its extreme precision. A sonomicrometer technique developed by Dr. Craig J. Hartley can detect changes in phase of as small as 1 degree of arc.sup.9. At 20 MHz this sonomicrometer can detect movement in a mouse carotid artery as minute as 1 micron.sup.ref This translates to a time resolution of 139 picoseconds.

b) Another novel sound speed method that could be used involves the incorporation into the catheter of a small chamber filled with an inert gas. As with the above H/H measurement by sound speed method, sound speed could be measured either by using the two-transducer (pitch catch) technique or utilizing the preferred transducer-reflector pair. Transit time measurements must be performed continuously at a rate of at least 30 cycles per second in order to detect all phases of systole and diastole. The zero pressure could be easily calibrated to atmospheric pressure prior to vascular insertion. Continuous temperature calibration would also be required, but is already being done continuously for the H/H monitor. This method could be more accurate and precise than solid state pressure sensors.

An advantage to using this method may stem from the fact that the sound speed analysis equipment is already incorporated into the system for H/H measurement. Applying this technique would require the addition of another transducer and reflector pair with the same electronics analyzing the signal. Potential disadvantages to this acoustic chamber approach may be that the close proximity of the chamber walls could result in anomalous sound speed readings. A lower frequency (50-500 KHz) transducer would be required for this technique. A potential pitfall could be the difficulty of developing a low frequency transducer that would be physically small enough to fit onto the catheter. Also, gas leakage could potentially limit the useful life of the monitor. If the gas did leak, it would not pose a danger to the patient because the volume of gas would so minute that it would immediately absorb into the blood. The type of gas utilized has yet to be determined and, except for safety reasons, would not be limited to any particular gas. Since instrument precision increases with frequency, the choice of gas used in this device would be dependent upon its ability to conduct higher acoustic frequencies. The particular frequency and gas characteristics are yet to be determined. The gas, of course, must not possess any properties that are toxic to the patient or that would deteriorate the plastic of the catheter itself.

C. Blood Flow Velocity Measurement

The arterial blood flow velocity parameter would be measured by use of a standard Doppler probe mounted at or near the tip of the catheter. The best mount position would be chosen in order to detect flow in a location where flow is unaffected by the presence of the catheter itself. It may be possible to obtain Doppler flow values using the same transducer as is used for the blood concentration measurement. The blood flow velocity measurement could be displayed continuously and it would be used to continuously calculate, display, and trend local vascular resistance or local vascular tone.

D. Calculation of Local Vascular Resistance (LVR)

It must be understood that by placing the device 120 multiparameter catheter into a peripheral vessel, total systemic vascular resistance (SVR) can not be obtained. SVR can only be accomplished by monitoring a central vessel. However, for purposes of trending SVR, the monitoring of a peripheral artery could be useful. Trends of LVR may parallel trends for SVR. It is possible to calculate vascular resistance or its inverse, vascular conductance, by using the measured values of blood pressure, flow velocity, and vessel cross-sectional area CSA. The mathematical relationships are as follows: [0153] F=V*CSA.sub.expressed in ml/min [0154] LVR=MAP/F.sub.expressed in mmHg/(ml/min) [0155] VC=F/MAP.sub.expressed in (ml/min)/mmHg where F is local blood flow volume in the peripheral artery, V is local blood flow velocity, and CSA is the cross-sectional area of the cannulated vessel, PVR is the local vascular resistance within the cannulated vessel, MAP is mean arterial pressure, and VC is vascular conductance.

The monitoring of these particular vascular system parameters would give the clinician valuable information on the general state of vascular tone. For example, when blood pressure plummets, generally there is compensation by sympathetic and adrenergic mechanisms to increase PVR in order to maintain adequate blood pressure. This is certainly true in the case of hemorrhagic shock, in which case device 120 would show an increasing PVR coupled with a decreasing blood pressure and possibly a decrease in vessel CSA. Conversely, when the vascular volume is restored via blood product and/or IV fluid administration, device 120 would show a returning to normal of the PVR from high levels. In the case of spinal shock, however, device 120 would show that normal compensatory mechanisms are not occurring and that PVR is inappropriately low given the current state of hypotension.

In reality, accurate intravascular measurement of vessel CSA may be cumbersome. It may be better to employ other techniques for vascular tone calculation. Device 120 could employ the use of pulse wave velocity (PWV) calculation to determine vascular tone. PWV in a region of an artery is mainly related to the elastic properties of the arterial wall of that region. Two techniques have been described by Harada et al that utilize one-point measurement of (PWV) and wave intensity (WI).sup.8. These two methods involve calculating 1) the characteristic impedance of an artery and 2) calculating the stiffness parameter. Interestingly, device 120 is already designed to measure the required input data for these equations including blood density, flow velocity, and pressure. Please see the reference article for the applicable equations.

E. Continuous Arterial Blood Gas Measurement

An example of an intravascular blood gas monitor that could potentially be incorporated into device 120 is NeoTrend made by Diametrics Medical, Inc, NeoTrend was evaluated in a journal article entitled "Continuous Neonatal Blood Gas Monitoring Using a Multiparameter Intra-arterial Sensor," by C. Morgan, S. J. Newell, D. A. Ducker, J. Hodgkinson, D. K, White, C. J. Morley, J. M. Church; "Arch Dis Child Fetal Neonatal Ed, March 1999; 80:F93-F98

Figure 6:
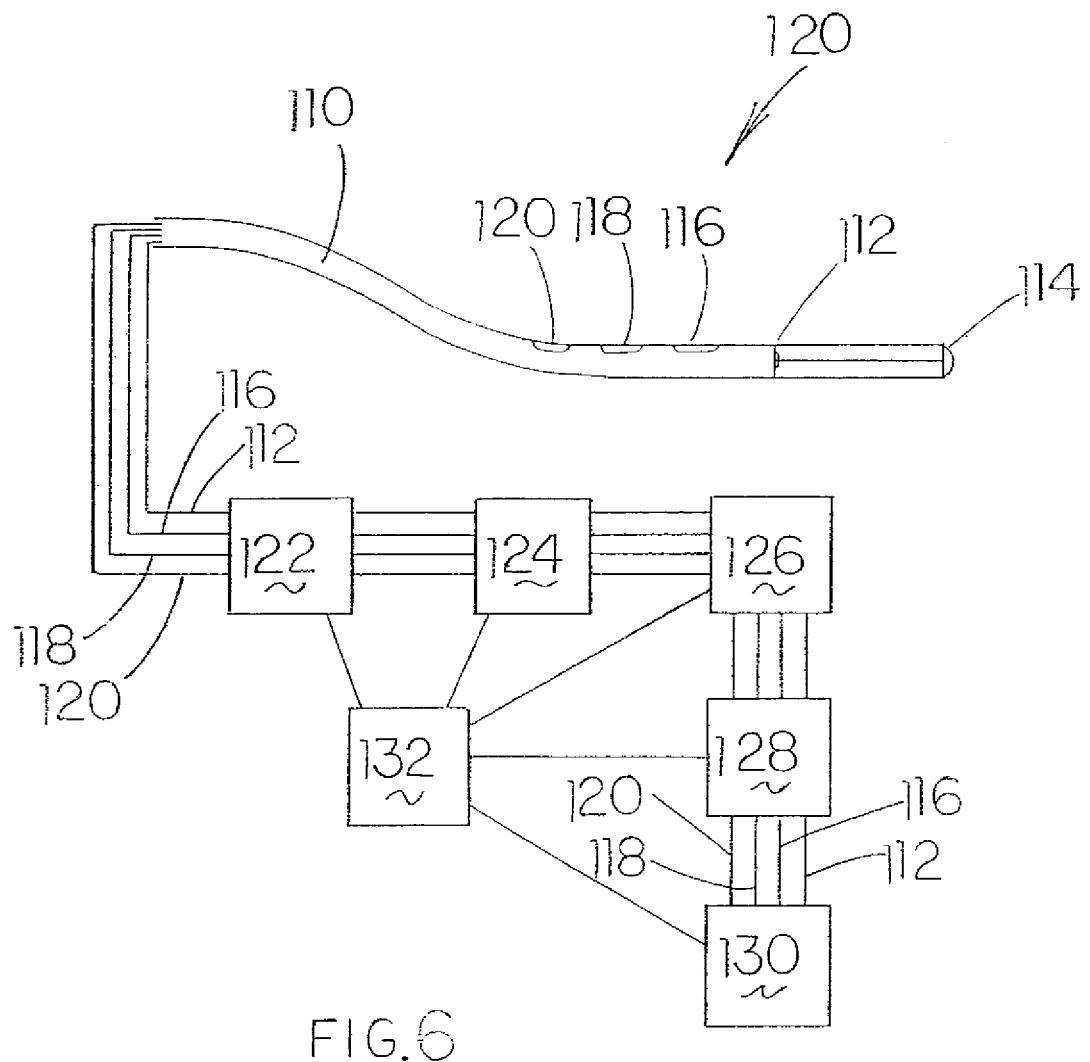
FIG. 6 is a diagrammatic view of the new and improved multiparameter intravascular catheter vital sign measurement device of the invention for the insertion into a blood vessel utilizing separate spaced apart transducers connected to drivers and recognition analysis devices.

FIG. 6 is a view of the new and improved multiparameter intravascular catheter 110 vital sign measurement device of the invention showing a single sender/receiver transducer 112 paired with a reflector 114. Another potential configuration with two transducers, one sender and one receiver, is not illustrated since the receiver transducer would simply occupy the location of the reflector in FIG. 6. Included are diagrammatic representations of the incorporated probes for measuring sound speed and blood flow 112-114, temperature 116, blood pressure (BP) 118, arterial blood gases (ABG's) 20.

Each of the sensors 12, 14, 16, 18, and 20 illustrated in FIG. 6 is connected to hardware drivers 22, and a computer 24 that is programmed with recognition and analysis software. Depending upon the function of the sensor 112, 116, 118, or 120, the computer software will differ as to each recognition and analysis computer 124 to receive the signal from its individual sensor 112, 116, 118, and 120, and convert the same into a measurement of blood concentration, hematocrit and/or hemoglobin, blood flow velocity, blood pressure, pulse rate, local vascular resistance, pH, pO2, pCO2 and any other data gathered from any other technology incorporated into the device. The display 128 will include both instantaneous measurements and a plot of each measurement versus time as it seems prudent to display for clinical use.

Scanners 126 are provided to scan each of the computers 124 sequentially from about 10 to 1000 times per second, depending upon the particular clinical application. Each of the scanners would be operatively connected to a display 128 that would display the measured data from each of the sensors 112, 116, 118, and 120 in the form of both instantaneous measurements and the historical trends of each parameter. Data derived mathematically, such as local vascular resistance and pulse pressure would likewise be displayed and trended. The display would be combined with selection switches by which each parameter and trend could be selectively displayed.

Attached to each display would be a printer 130 which would be capable of printing current vital parameters and a continuous record of trends and rate of change of each measurement or calculated parameter.

Each of the sensors 112, 116, 118, and 120, the hardware drivers 122, each of the recognition and analysis computers 124, each of the scanners 126, each of the displays 128, and each of the printers 130 are connected to a power source 132.

Figure 7:
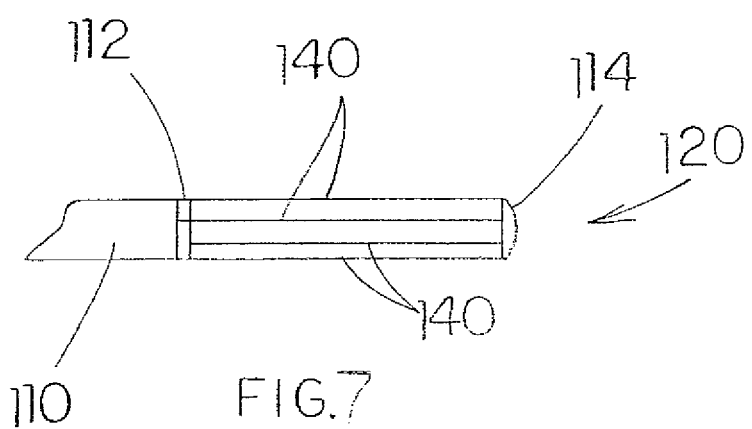
FIG. 7 illustrates another version of the new and improved multiparameter intravascular catheter vital sign measurement device of the invention showing a transducer/receiver with a reflector held apart by struts.

FIG. 7 illustrates a potential configuration for the sound speed sensor with transducer 112 and reflector 114 held apart by stainless steel struts 140. The scale image provides an example of a catheter 110 that is 1 mm diameter and the transducer-reflector separation is 5 mm. The actual dimensions of the catheter may vary according to the particular logistics of construction and function, and are not limited to these dimensions.

Figure 8:
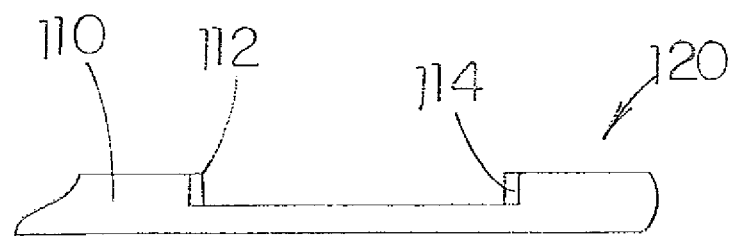
FIG. 8 is a view like FIG. 7 showing still another version of the new and improved multiparameter intravascular catheter vital sign measurement device of the invention showing a single sender/receiver transducer and a reflector mounted at opposite ends of a notch cut into the side of the catheter.

FIG. 8 illustrates another potential configuration for the sound speed sensor with transducer 112 and reflector 114 mounted at opposite ends of a notch cut into the side of the catheter 110.

The particular form(s) that these sound speed measurement devices might assume are not limited and would include any configuration that would allow intravascular measurement of speed of sound in whole blood.

FIG. 9 illustrates a potential configuration of the gas-filled chamber pressure sensor. This particular example shows transducer 134 and reflector 136 mounted in a notch cut into the side of the catheter 110, with a membrane or diaphragm 138 covering and sealing the gas-filled chamber 142. The transducer-reflector separation is 5 mm in this example. The actual dimensions of the chamber, the particular transducer frequency, and type of gas used may vary according to the particular logistics of construction and function. The particular forms that the this sound speed measurement device might assume are not limited and would include any configuration that would allow measurement of the speed of sound in any gas contained within any intravascular device.

The new and improved multiparameter intravascular catheter vital sign measurement device 120 of the invention is a medical device for supplying multiple physiologic and hemodynamic parameter measurements for any clinical medicine, veterinary, military, or research setting where such information is useful to clinicians conducting physical examinations, or monitoring or treating patients or personnel. It would be especially useful in the care of critically ill or injured patients.

When the device is placed intraarterially, it would be capable of accurately and continuously measuring arterial blood pressure, pulse rate, blood density, H/H, temperature, and blood flow velocity without the usual hydraulic arterial-line system, and it would also be capable of trending a calculated local vascular resistance. Vascular volume could be obtained by a common dilution method. When the device is placed intravenously, blood concentration, H/H, and temperature would be continuously monitored.

In addition, device 120 could incorporate any existing or future available intravascular technology for physiologic and hemodynamic measurements which might be desirable to monitor in the various environments discussed above. Examples of desirable venous or arterial physiologic parameters include, but are not limited to, pO2, pCO2, pH, lactic acid levels, electrolytes, PT, PTT. Future advances in technology could bring the eventual incorporation into the catheter of such entities as genetic testing or blood-typing for cross-match for anticipated transfusion. In addition to its value in critical care medicine, the device could have many other uses, including but not limited to use in many types of medical or veterinary research, in clinicians' offices, in military, aerospace, and subsurface marine applications, and in cardiovascular and pharmacological research.

Potentially, any other conventional equipment that can be miniaturized could be mated with the device in order to continuously monitor a multitude of desirable physiologic parameters. The particular existing and available technology that may be incorporated into device 120 will depend upon the amenability of each individual parameter to miniaturization and to its accuracy, precision, licensing and safety restrictions, and compliance to specific regulatory guidelines.

F. LITERATURE CITED (1) Hingohofer-Szalkay, J E Greenleaf, Continuous monitoring of blood volume changes in humans. J Appl Physiol. 1987; 63: 1003-7 [0173] (2) Hinghofer-Szalkay H. Continuous blood densityometry: Fluid shifts after graded hemorrhage in animals. Am J Physiol 1986; 250 (Heart Circ. Physiol. 19): H342-50 [0174] (3) Hinghofer-Szalkay H., Koenig E, Schmied J, Heimel H. A new principle for dynamic fluid shift investigations in astronauts. Proc 4.sup.th Eur Symp Life Sci in Space: esa sp-307, 129-132, 1990. [0175] (4) Watenpaugh, D E, and Hargens A R. The cardiovascular system in microgravity. In: Handbook of Physiology. Environmental Physiology Bethesda, Md.: Am Physiol. Soc, 1996, sect. 4, vol. 1, chapt. 29, p. 631-674 [0176] (5) Quick, C M, Berger D S, and Noordergraaf A. Apparent arterial compliance. AM J Physiol Heart Cire Physiol 274: H1393-H1401, 1998 [0177] (6) S. M. Tibby and I. A. Murdoch. Monitoring cardiac function in intensive care. Archives of Disease in Childhood 2003; 88:46-52 [0178] (7) Bakke, T., Gytre, T., Haagensen, A., & Giezendanner, L. (1975). Ultrasonic measurement of sound velocity in whole blood: A comparison between an ultrasonic method and the conventional packed-cell-volume test for hematocrit determination. Scandinavian Journal of Clinical Laboratory Investigations, 35(5), 473-478. Abstract retrieved Feb. 5, 2005, from PubMed database. [0179] (8) Harada, A., Okada, T., Sugawara, M., & Niki, K. (2000). Development of a non-invasive real-time measurement system of wave intensity. IEEE Ultrasonics Symposium. [0180] (9) Hartley, C. J., Reddy, A. K., Madala, S., Entman, M. L., Michael, L. H., & Taffet, 3. E. (2004). Non-invasive ultrasonic measurement of arterial wall motion in mice. American Journal of Physiology—Heart and Circulator Physiology, 10, 1426-1432. [0181] (10) Hinghofer-Szalkay, H., Haas, G., Oser, H., & Kenner, T. (1989). Monitoring fluid shifts in humans: Application of a new method. Aviation & Space Environmental Medicine, 60(1), 23-28. Abstract retrieved Dec. 5, 2003 from PubMed database. [0182] (11) Johner, C., Chamney, P. W., Schneditz, D., & Kramer, M. (1998). Evaluation of an ultrasonic blood volume monitor. Nephrology Dialysis Transplantation, 13, 2098-2103. [0183] (12) Kenner, T. (1996). The continuous measurement of blood density and its experimental and clinical application—a review. Retrieved Sep. 27, 2003, from http://www.k-funigraz.ac.at [0184] (13) Millero F. J. and Xu Li, Comments on "On equations for the speed of sound in seawater" (1994), J. Acoust. Soc. Am. 95(5), pp 2757-275 [0185] (14) Mo, L. Y. L. & Cobbold, R. S. C. (1992). A unified approach to modeling the backscattered Doppler ultrasound from blood. IEEE Transactions on Biomedical Engineering, 39(5), 450-461. [0186] (15) Secomski, W., Nowicki, A., Guidi, F., Tortoli, P., & Lewin, P. A. (2003). Noninvasive in vivo measurements of hematocrit. Journal of Ultrasound Medicine, 22(4), 375-384. Abstract retrieved Jan. 14, 2005, from PubMed database. [0187] (16) http://ioc.unesco.org/oceanteacher/resourcekit/M3/Converters/SeaWaterEquationOfState/Sea%20Water%20Equation%20of%20State%20Calculator.htm).

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. An apparatus for continuously monitoring arterial blood pressure comprising:
   an intravascular catheter having a chamber filled with a fluid;
   a transducer disposed in the chamber, wherein the transducer is configured to periodically transmit an ultrasound signal that propagates through the fluid;
   a reflector disposed in the chamber and spaced apart from the transducer, wherein the transducer is configured to detect at least a portion of the signal that is reflected from the reflector; and
   an analysis device configured to determine speed of sound through the fluid in the chamber based on transit times of the signals periodically transmitted between the transducer and reflector, wherein the analysis device is configured to continuously determine an arterial blood pressure using an equation defining a relationship between the arterial blood pressure and based on the measured speed of sound through the fluid in the chamber.

2. The apparatus of claim 1, wherein the fluid in the chamber is an inert gas.

3. The apparatus of claim 2, wherein the signal transmitted by the transducer has a frequency between approximately 50 Hz and 500 kHz.

4. The apparatus of claim 3, wherein the transducer transmits the signal at least 30 times per second.

5. An apparatus for continuously monitoring arterial blood pressure comprising:
- an intravascular catheter having a chamber filled with a fluid;
- one or more transducers disposed in the chamber that are configured to periodically transmit ultrasound signals in the chamber, wherein the one or more transducers are configured to detect transit times of the ultrasound signals between a first location and a second location in the chamber, wherein the fluid in the chamber is of the type that transit times between the first location and the second location are influenced by changes in pressure of blood flowing proximate the chamber; and
- an analysis device configured to determine speed of sound through the fluid in the chamber based on transit times of the signals periodically transmitted between the transducer and reflector, wherein the analysis device is programmed with an equation that defines a relationship between an arterial blood pressure and the measured speed of sound through the fluid, wherein the analysis device is configured to continuously determine the arterial blood pressure based on the measured speed of sound through the fluid.

6. The apparatus of claim 5, wherein the fluid in the chamber is an inert gas.

7. The apparatus of claim 6, wherein the signals transmitted by the one or more transducers has a frequency between approximately 50 Hz and 500 kHz.

8. The apparatus of claim 7, wherein the one or more transducers transmit the signal at least 30 times per second.

9. An apparatus for continuously monitoring arterial blood pressure comprising:
- an intravascular catheter having a chamber filled with a fluid;
- one or more transducers disposed in the chamber that are configured to periodically transmit ultrasound signals in the chamber, wherein the one or more transducers are configured to measure speed of sound in the chamber by detecting time of flight of the ultrasound signals through the fluid between a first location and a second location, wherein the fluid in the chamber is of the type that time of flight between the first location and the second location are influenced by changes in pressure of blood flowing proximate the chamber; and
- an analysis device programmed with an equation defining a relationship between an arterial blood pressure and the speed of sound measurement, wherein the analysis device is configured to continuously determine the arterial blood pressure based on the speed of sound measured by the one or more transducers in the chamber.

10. The apparatus of claim 9, wherein the fluid in the chamber is an inert gas.

* * * * *